US011827403B2

(12) United States Patent
Boira Bonhora et al.

(10) Patent No.: US 11,827,403 B2
(45) Date of Patent: Nov. 28, 2023

(54) METHOD FOR THE ASEPTIC FILLING OF A BAG

(71) Applicant: GRIFOLS, S.A., Barcelona (ES)

(72) Inventors: Jordi Boira Bonhora, Barcelona (ES); Miquel Faba Vilella, Barcelona (ES); Daniel Fleta Coit, Barcelona (ES)

(73) Assignee: GRIFOLS, S.A., Barcelona (ES)

( * ) Notice: Subject to any disclaimer, the term of this patent is extended or adjusted under 35 U.S.C. 154(b) by 426 days.

(21) Appl. No.: 16/807,948

(22) Filed: Mar. 3, 2020

(65) Prior Publication Data

US 2020/0198820 A1 Jun. 25, 2020

Related U.S. Application Data

(62) Division of application No. 14/919,110, filed on Oct. 21, 2015, now Pat. No. 10,625,894.

(30) Foreign Application Priority Data

Oct. 23, 2014 (ES) ............................... ES201431561

(51) Int. Cl.
*A61J 1/10* (2006.01)
*A61J 1/14* (2023.01)
(Continued)

(52) U.S. Cl.
CPC ................. *B65B 55/08* (2013.01); *A61J 1/10* (2013.01); *A61J 1/1412* (2013.01); *A61J 1/1431* (2015.05); *A61J 1/1475* (2013.01); *A61J 1/1481* (2015.05); *B65B 3/003* (2013.01); *B65B 7/02* (2013.01); *B65B 51/225* (2013.01)

(58) Field of Classification Search
CPC ......... A61J 1/10; A61J 1/1412; A61J 1/1431; A61J 1/1475; A61J 1/1481; A61J 1/1406; B65D 51/002; B29C 66/1312; B29C 65/02
See application file for complete search history.

(56) References Cited

U.S. PATENT DOCUMENTS 3,564,805 A 2/1971 Mumford
4,187,893 A * 2/1980 Bujan .................. A61J 1/1406 604/408
(Continued)

FOREIGN PATENT DOCUMENTS

CA 2884719 A1 2/2014
DE 19617024 A1 11/1997
(Continued)

OTHER PUBLICATIONS

English Translation of description for Iwasaki et al. (JP 2009132431). (Year: 2009).*
(Continued)

*Primary Examiner* — Ariana Zimbouski
(74) *Attorney, Agent, or Firm* — Dinsmore & Shohl LLP

(57) ABSTRACT

Method for the aseptic filling of a bag with a pharmaceutical product or liquid which comprises the following steps: a) a first step in which the cap is inserted in the inlet of the bag; b) a second step in which said cap is raised and the pharmaceutical product or liquid concerned is introduced; c) a third step in which the cap is re-inserted in the inlet of the bag; and d) a fourth step in which the cap and the inlet of the bag are welded.

12 Claims, 24 Drawing Sheets

(51) Int. Cl.

| | |
|---|---|
| ***B65B 55/08*** | (2006.01) |
| ***B65B 3/00*** | (2006.01) |
| ***B65B 7/02*** | (2006.01) |
| ***B65B 51/22*** | (2006.01) |

(56) References Cited

U.S. PATENT DOCUMENTS

| | | | | |
|---|---|---|---|---|
| 4,200,209 | A * | 4/1980 | Aguettant .......... | B29C 66/1312 222/541.6 |
| 5,509,433 | A | 4/1996 | Paradis | |
| 5,762,646 | A | 6/1998 | Cotter | |
| 6,029,946 | A | 2/2000 | Doyle | |
| 6,145,688 | A | 11/2000 | Smith | |
| 6,256,964 | B1 | 7/2001 | Drevfors | |
| 6,485,479 | B1 | 11/2002 | Knierbein | |
| 6,629,401 | B1 | 10/2003 | Hins et al. | |
| 10,625,894 | B2 * | 4/2020 | Boira Bonhora ..... | A61J 1/1481 |
| 2004/0026432 | A1 | 2/2004 | Matsumura et al. | |
| 2004/0141886 | A1 | 7/2004 | Py et al. | |
| 2004/0267228 | A1 | 12/2004 | Hattori et al. | |
| 2005/0035149 | A1 | 2/2005 | Curutcharry | |
| 2005/0059952 | A1 | 3/2005 | Giuliano et al. | |
| 2005/0102978 | A1 | 5/2005 | Gueret | |
| 2005/0121103 | A1 * | 6/2005 | Steigerwalt .......... | A61M 39/24 141/100 |
| 2006/0013974 | A1 | 1/2006 | Mizuo et al. | |
| 2006/0138069 | A1 * | 6/2006 | Domkowski ............ | A61J 1/10 215/247 |
| 2007/0214748 | A1 | 9/2007 | Dovesi | |
| 2008/0066824 | A1 | 3/2008 | Py | |
| 2009/0235619 | A1 | 9/2009 | Ostler et al. | |
| 2009/0314781 | A1 | 12/2009 | Paul | |
| 2012/0284991 | A1 * | 11/2012 | Kusz .................... | A61M 39/12 137/315.01 |
| 2015/0238387 | A1 | 8/2015 | Caetano | |

FOREIGN PATENT DOCUMENTS

| | | | | |
|---|---|---|---|---|
| EP | 0 731 037 | A1 | | 9/1996 |
| EP | 0830874 | | * | 3/1998 |
| ES | 2166034 | T3 | | 4/2002 |
| JP | 2009-132431 | A | | 6/2009 |
| JP | 2009132431 | A | * | 6/2009 |
| JP | 2014156797 | | * | 8/2014 |
| WO | 2004033954 | A2 | | 4/2004 |
| WO | 2006/071781 | A2 | | 7/2006 |

OTHER PUBLICATIONS

Communication, dated Nov. 16, 2016, in European Patent Application No. 15382510.4, 5 pages.

Third-Party Observation, dated Feb. 3, 2017, in European Patent Application No. 15382510.4, 6 pages.

Extended European Search Report for EP Application No. 15382510.4, European Patent Office, The Hague, Netherlands, completed on Feb. 24, 2016, 8 pages.

* cited by examiner

METHOD FOR THE ASEPTIC FILLING OF A BAG

CROSS-REFERENCE TO RELATED APPLICATIONS

This application is a divisional of U.S. patent application Ser. No. 14/919,110, filed Oct. 21, 2015, and published Apr. 28, 2016, as U.S. 2016/0114922, which claims priority under U.S.C. § 119 to Spanish Application No. P201431561, filed Oct. 23, 2014, the contents of which are incorporated by reference in their entirety herein.

DESCRIPTION

The present invention relates to the pharmaceutical sector, specifically to a method that allows the aseptic filling of bags with pharmaceutical products.

In the pharmaceutical industry it is essential to have methods available not only for the manufacture of aseptic containers but also for the aseptic filling thereof.

In addition, in the pharmaceutical industry it is preferable to have flexible methods with steps that do not necessarily and inevitably have to be carried out one immediately after the other. In other words, if necessary, there are steps in said method in which it can be stopped for a given period of time without adversely affecting the final product.

There are numerous methods and variants thereof in the prior art for the manufacture of all kinds of aseptic containers for use in the pharmaceutical industry.

However, the known prior art concerning the aseptic filling of said containers, specifically, aseptic bags, is much more limited. The aseptic filling of bags is generally carried out through one of the sides thereof, not through the inlet positioned in the bags. In other words, the aseptic filling methods of the prior art produce bags by welding the inlet to two sheets made of the selected material and welding said sheets at three of the edges thereof (the one that contains the inlet and two additional edges) and the pharmaceutical product or liquid concerned is introduced through the edge that remains open and which is then welded. Using this method involves various risks that can affect the quality and final properties of the pharmaceutical product or liquid. The large opening of the bag used for filling increases the possibility of the welding process affecting the pharmaceutical product or liquid:

a) directly: there is an increased possibility of biological contamination of the end product occurring and, when the welding method (using heat or ultrasound, for example) is applied to a surface in the vicinity of the product, a somewhat aggressive method is being used over a large surface and there is therefore a possibility of the physical, biological properties and the appearance or colour of the end product being affected. In addition, drops of the pharmaceutical product or liquid may also remain adhered to the wall of the bag, which drops are directly affected during the welding process. Said drops will subsequently come in contact with the rest of the pharmaceutical product or liquid and might therefore alter the physical, biological properties and the appearance or colour of the end product; or b) indirectly: during the welding process, particles might be produced from the welded surfaces and said particles could contaminate the end product changing its physical, biological properties and appearance or colour.

The German patent application DE19617024A1 discloses an inlet/cap structure and a method for the aseptic filling of bags based on filling the bag through the inlet and then welding the cap, which claims to attempt to overcome the problems mentioned above. However, it does not fully resolve all the problems mentioned because it discloses a structure and a method that do not provide flexibility in time and space for the steps of the bag filling method; and the inlet/cap structure disclosed does not allow to ensure that the pharmaceutical product or liquid is not contaminated or affected by particles produced during the welding process.

There is therefore still a need for a simple, scalable and flexible (in time and space) method for the aseptic filling of bags with pharmaceutical products or liquids and that provides aseptic filling of the bag, minimising or eliminating the risk of biological contamination or contamination by particles (generated during the welding process) of the pharmaceutical product or liquid, preserving the appearance or colour and the physical and biological characteristics of said pharmaceutical product or liquid.

The inventors have carried out extensive studies and have developed a simple method that can be applied on a large scale and that allows the aseptic filling of bags with pharmaceutical products or liquids which overcomes all said problems present in the prior art.

In a first aspect of the present invention a method for the aseptic filling of bags with pharmaceutical products or liquids is therefore disclosed.

In an additional aspect, the present invention discloses an inlet/cap structure that comprises an inlet and a cap and has two closure positions.

In another aspect, the present invention relates to the use of an inlet/cap structure, as disclosed in the present document, for carrying out the method for the aseptic filling of bags with pharmaceutical products or liquids of the present invention.

In another additional aspect, the present invention discloses a bag that comprises at least one inlet/cap structure according to the present invention, that is, an inlet/cap structure that comprises an inlet and a cap and that has two closure positions.

In another aspect, the present invention discloses the use of a bag that comprises an inlet/cap structure, as disclosed in the present document, in the method for the aseptic filling of bags with pharmaceutical products or liquids of the present invention.

In an additional aspect, the present invention discloses the use of the method of the present invention to maintain or preserve the colour, appearance and/or physical and/or biological properties of a pharmaceutical product or liquid during the method for the aseptic filling of bags with said pharmaceutical products or liquids.

In an additional aspect, the present invention discloses the use of the method of the present invention to prevent contamination of a pharmaceutical product or liquid during the method for the aseptic filling of bags with said pharmaceutical product or liquid.

In an additional aspect, the present invention relates to a bag filled with a pharmaceutical product or liquid filled by any of the methods of the present invention described in the present document.

As used in the present document, the term "hermetic closure" and its plural refers to a type of closure that allows the inside of a bag to be isolated from the outside and that is therefore able to maintain the sterile and aseptic conditions of said bag interior.

Therefore as mentioned earlier, the present invention relates to a method for the aseptic filling of a bag with a pharmaceutical product or liquid characterised in that it comprises the following steps:

a) A first step in which the cap is inserted in the inlet of the bag producing or providing a hermetic closure therebetween;

b) a second step in which said cap is raised and the pharmaceutical product or liquid concerned is introduced;

c) a third step in which the cap is re-inserted in the inlet of the bag producing or providing a hermetic closure therebetween; and d) a fourth step in which the cap and the inlet of the bag are welded, in which bags are used that comprise at least one inlet/cap structure which comprises an inlet and a cap, and which has two closure positions, a first position which consists of a reversible hermetic closure and a second position which consists of a final or irreversible hermetic closure by welding, and in which at least the second and third steps (steps b) and c) respectively), are carried out in a sterile environment.

With the method of the present invention the problems present in the prior art mentioned earlier are overcome. This is because the hermetic closure allows the sterile and aseptic conditions inside of the bag to be maintained and thus of the contents thereof. The method of the present invention therefore provides flexibility in space and time.

It provides flexibility in space because the first step (step a)) can or could be carried out in a different place from that used for the second and third steps (steps b) and c) respectively). The fourth step (step d)) can or could also be carried out in a different place from that used for the first, second and third steps (steps a), b) and c) respectively).

Flexibility in time is achieved because the method of the present invention can be paused or stopped for a given period of time before it is completed at at least two points with no risk of the bag being contaminated (and therefore no need for a new sterilisation stage thereof), nor of the pharmaceutical product or liquid introduced therein being contaminated after the first step (step a)) and/or after the third step (step c)).

In addition, the method of the present invention allows the aseptic filling and welding of the bags with the pharmaceutical product or liquid of interest, thus preventing biological contamination of the end product.

Moreover, the inlet/cap structure used and required to complete or carry out the method of the present invention, as will be seen in more detail below, allows preventing not only the biological contamination of the pharmaceutical product or liquid introduced into the bag, but also preventing contamination of the pharmaceutical product or liquid by particles derived or resulting from the welding process.

In a preferred embodiment, the pharmaceutical product or liquid is a liquid of biological origin, more preferably, blood or products derived from blood such as plasma, serum, red blood cell solution, albumin solution, α1-antitrypsin solution, von Willebrand factor solution, solution comprising coagulation factors such as factor VII, factor VIII and factor IX, immunoglobulin solution, plasminogen solution, plasmin solution, antithrombin III solution, fibrinogen solution, fibrin solution, thrombin solution or combinations thereof. It is also envisaged that the pharmaceutical product or liquid is not of biological origin but is obtained by any other process or method known in the prior art, such as chemical synthesis, recombinant production or transgenic production. Therefore in another preferred embodiment the proteins of the solutions of albumin, α1-antitrypsin, von Willebrand factor, coagulation factors such as factor VII, factor VIII and factor IX, immunoglobulins, plasminogen solution, plasmin solution, antithrombin III solution, fibrinogen solution, fibrin solution, thrombin solution or combinations thereof can be obtained by chemical synthesis, by recombinant production or by transgenic production thereof by any of the methods known in the prior art. In the most preferred embodiment, the pharmaceutical product or liquid is an albumin solution of biological origin, produced by chemical synthesis or obtained by recombinant or transgenic production, preferably of biological origin.

In another preferred embodiment, the bag has a single inlet/cap structure of the present invention with the characteristics mentioned earlier, that is, a structure that comprises an inlet and a cap and that has two closure positions, a first position which consists of a reversible hermetic closure and a second position which consists of a final or irreversible hermetic closure by welding.

In the second step (step b)) any volume of the pharmaceutical product or liquid can be introduced into the bag. In an additional embodiment, the volume of pharmaceutical product or liquid introduced into the bag is between 1% and 100% of the total volume of the bag.

In another preferred embodiment, in the fourth step (step d)) the weld between the cap and the inlet of the bag is produced by any method known in the prior art. In a more preferred embodiment the weld is produced using heat or ultrasound, most preferably, ultrasound.

In addition, in the fourth step (step d)), the weld effected is produced between a flange present on the inlet and a flange present on the cap. Said weld may affect the whole of the lower surface of the cap flange and the upper surface of the inlet flange or only a portion of said surfaces. It is envisaged that said surfaces may or may not be completely conjoined. Depending on said conjunction, the contact surface between the cap and inlet flanges will be larger or smaller. If said weld only affects a portion of the lower and upper surface of the cap and inlet flanges respectively, said weld at least surrounds the channel present in the inlet. In a preferred embodiment, the weld between the cap and the inlet is produced in a strip in which the cap flange comprises at least one projection or crown on its lower surface and the inlet flange comprises at least one recess on the upper surface thereof, both positioned at the periphery and continuously surrounding the channel present on each of the corresponding parts (inlet and cap). Alternatively, in another preferred embodiment, it is also envisaged that the at least one projection or crown should be present on the inlet flange and the at least one recess on the cap flange. In one of the most preferred embodiments, the weld between the cap and the inlet is produced in a strip in which the cap flange comprises a projection or crown and the inlet flange comprises a recess, both positioned at the periphery and continuously surrounding the channels present in the corresponding parts. In the other most preferred embodiment, the weld between the cap and the inlet is produced in a strip in which the cap flange comprises a recess and the inlet flange comprises a projection or crown, both positioned at the periphery and continuously surrounding the channels present in the corresponding parts.

In another preferred embodiment, the method of the present invention comprises an additional step. Said additional step can be positioned or located either before the first step of the method (step a)) or between the first and second steps (steps a) and b) respectively). In this additional step, the bag which comprises the at least one inlet/cap structure (with the cap inserted in the inlet or not depending on where the additional step is positioned) is sterilised. Said sterilisation is carried out by any known method of the prior art, more preferably using ultraviolet radiation, electron radiation (e-beam) or gamma radiation. In a preferred embodiment, the radiation used in said irradiation processes is 25-35 kGy.

The sterile environment in which the second and third steps (steps b) and c) respectively) is carried out may be any of those known in the prior art that allow the sterility and asepsis of the bag to be maintained during the method of the present invention and, consequently, of the pharmaceutical product or liquid introduced therein. In the most preferred embodiment, said sterile environment is achieved using horizontal laminar flow.

In another preferred embodiment, the first and/or fourth steps (steps a) and d) respectively) are also carried out in a sterile environment. Said sterile environment, as mentioned earlier, may be any of those known in the prior art that allow the sterility and asepsis of the bag to be maintained during the method of the present invention and, consequently, of the pharmaceutical product or liquid introduced therein, more preferably, the sterile environment is achieved using horizontal laminar flow.

As mentioned earlier, the present invention also relates to or discloses an inlet/cap structure which comprises an inlet and a cap and which has two closure positions, characterised in that the first closure position consists of a reversible hermetic closure and the second one consists of a final or irreversible hermetic closure by welding.

To achieve said closures between the inlet and the cap, said structures have flanges with surfaces that are conjoined totally or in part (the conjunction takes place between the lower surface of the cap flange and the upper surface of the inlet flange). Thus, in one embodiment, the lower surface of the cap flange and the upper surface of the inlet flange are completely conjoined. In another embodiment, said surfaces are conjoined in part. Said aforementioned total or partial conjunction may take several forms provided that when the cap is correctly positioned on the inlet, contact points, surfaces or strips are established between said structures which contribute to maintain the sterility and asepsis of the inside of the bag during the aseptic filling method of the present invention (hermetic closure) and are used to effect the welding process mentioned in step four (step d)) of the method of the present invention. In one of the most preferred embodiments, the lower surface of the cap flange comprises a continuous projection situated at or near the periphery thereof, that is, a crown located at or near the periphery of said flange; and the upper surface of the inlet flange comprises a continuous recess situated at or near the periphery thereof, so that when the cap is placed, inserted or fixed in the inlet, said projection and recess fit together and establish a contact strip. In the other more preferred embodiment, the upper surface of the inlet flange comprises a continuous projection situated at or near the periphery thereof, that is, a crown located at or near the periphery of said flange; and the lower surface of the cap flange comprises a continuous recess situated at or near the periphery thereof, so that when the cap is placed, inserted or fixed in the inlet, said projection and recess fit together and establish a contact strip.

Said contact points, surfaces or strips (preferably a contact strip) are used both to isolate the outside of the bag from the inside and, in the fourth step (step d)) of the method of the present invention, to perform the welding of the inlet and the cap, that is, the flanges present on the inlet and the cap contribute to perform the second closure position, the weld between the inlet and the cap (final or irreversible hermetic closure by welding).

In addition, as mentioned earlier, said flanges also contribute to the first hermetic closure that takes place between the inlet and the cap (produced by interference when fitting the cap in the inlet).

The above-mentioned inlet and cap flanges may take different forms, even said forms possibly being the same as each other or different. In the same way, the flanges present on the inlet and the cap may be the same size or different sizes. In the most preferred embodiment, the cap flange and the inlet flange have the same oval form. In another preferred embodiment, said flanges are the same, or approximately the same, size.

It is also envisaged that the inlet and the cap of the inlet/cap structure of the present invention are made of the same material or of different materials. In a preferred embodiment both parts are made of the same material, and even more preferably, both parts are made of polyethylene.

As mentioned earlier, the inlet has a channel. In a preferred embodiment said channel does not have physical barriers and passes vertically through the inlet, that is, once placed in a bag, there would be no physical barriers between the inside and the outside of said bag unless a cap is placed in said inlet, which makes filling through said channel easier.

In addition, it is also envisaged that the cap comprises a channel. In a preferred embodiment, the channel of the cap comprises a physical barrier so that once the cap has been fixed or inserted in the inlet of the bag, the sterility and asepsis of the inside of the bag can be maintained. In an even more preferred embodiment, said physical barrier is a membrane which seals the channel of the cap. It is envisaged that the membrane is broken or perforated when the bag is used, in order to remove the pharmaceutical product or liquid contained therein. Said membrane is commonly used in the inlets of the prior art and the characteristics and composition thereof are therefore known to persons skilled in the art. In a more preferred embodiment, said membrane has a thickness of between 0.2 mm and 0.4 mm and is made of polyethylene. The membrane may be positioned at any height in the channel of the cap, more preferably in the distal portion. Normally, said membrane is broken or passed through when the bag is used in order to remove the contents of the bag (a pharmaceutical product or liquid), or to introduce an additional compound or liquid into the bag in order to use the contents thereof at a later stage.

Said cap may comprise in its proximal portion an actuation key which can be withdrawn or removed by the user rotating it. Said structure helps maintain the sterility of the bag until it is used, when it is withdrawn or removed (it is a protective structure that is only removed when the bag is to be used).

Once said structure has been removed a punch or needle can be inserted through the membrane situated in the above-mentioned cap, in order to access, extract and use the pharmaceutical product or liquid contained in the bag.

The inlet/cap structure of the present invention, as mentioned earlier, comprises means for producing a reversible hermetic closure (first closure position) between the inlet and the cap. In addition, and preferably, the reversible hermetic closure produced by said means is placed between the welding zone between the flanges and the contents of the bag, preventing or contributing to prevent any loose particles produced during the welding process from entering.

Said hermetic closure may be produced by any known means or methods of the prior art. In a preferred embodiment, said reversible hermetic closure is produced by the pressure caused by the dimensional interference between the channel of the inlet and a distal extension of the cap that remains inserted in said channel, so that the outer surface of said distal extension is in contact with the inner surface of the channel of the inlet, contributing to the hermetic closure between the cap and the inlet. Thus, the reversible hermetic closure produced between the distal extension of the cap and the channel of the inlet is placed between the welding zone (contact strip) and the contents of the bag, thus preventing, or contributing to prevent, any loose particles produced during the welding process from entering.

The outer surface of the above-mentioned distal extension of the cap and the inner surface of the channel of the inlet may be of any type known in the prior art provided the contact thereof allows or contributes to producing a reversible hermetic closure. In a preferred embodiment, said surfaces are smooth with no projections.

In another preferred embodiment, said surfaces are cylindrical surfaces, which allows the reversible hermetic closure to be opened and closed by means of linear movements in the direction of the central axis of the inlet channel.

In addition, said distal extension may continue with said cap channel. Therefore in another preferred embodiment, said membrane is located in this distal extension present in the cap, preferably in the distal zone of said extension.

As mentioned earlier, the present invention also relates to the use of an inlet/cap structure as disclosed in the present document in the method for the aseptic filling of bags with pharmaceutical products or liquids of the present invention.

In another additional aspect, as mentioned earlier, the present invention relates to a bag which comprises at least one inlet/cap structure of the present invention as described in the present document, that is, an inlet/cap structure which comprises an inlet and a cap and which has two closure positions, in which the first closure position consists of a reversible hermetic closure and the second consists of a final or irreversible hermetic closure by welding.

In the present invention, the bag that will contain the pharmaceutical product or liquid and which will be used in the method of the present invention, can be made of any material appropriate for the pharmaceutical industry known in the prior art. In a preferred embodiment, the bag is made of polyethylene.

In another preferred embodiment, the bag comprises a single inlet/cap structure of the present invention.

In addition, the bag may comprise other additional inlets or structures.

In a preferred embodiment, the pharmaceutical product or liquid is a liquid of biological origin, more preferably, blood or products derived from blood such as plasma, serum, red blood cell solution, albumin solution, α1-antitrypsin solution, von Willebrand factor solution, solution comprising coagulation factors such as factor VII, factor VIII and factor IX, immunoglobulin solution, plasminogen solution, plasmin solution, antithrombin III solution, fibrinogen solution, fibrin solution, thrombin solution or combinations thereof. It is also envisaged that the pharmaceutical product or liquid is not of biological origin but is obtained by any other process or method known in the prior art, such as chemical synthesis, recombinant production or transgenic production. Therefore in another preferred embodiment the proteins of the solutions of albumin, α1-antitrypsin, von Willebrand factor, coagulation factors such as factor VII, factor VIII and factor IX, immunoglobulins, plasminogen solution, plasmin solution, antithrombin III solution, fibrinogen solution, fibrin solution, thrombin solution or combinations thereof can be obtained by chemical synthesis, by recombinant production or by transgenic production thereof by any of the methods known in the prior art. In the most preferred embodiment, the pharmaceutical product or liquid is an albumin solution of biological origin, produced by chemical synthesis or obtained by recombinant or transgenic production, preferably of biological origin.

The methods for aseptically producing a bag comprising at least one inlet/cap structure with the characteristics mentioned above are known in the prior art.

As mentioned earlier, the present invention also relates to the use of a bag which comprises an inlet/cap structure as disclosed in the present document in the method for the aseptic filling of bags with pharmaceutical products or liquids of the present invention.

As mentioned earlier, the present invention also discloses the use of the method of the present invention to maintain or preserve the colour and/or biological properties of a pharmaceutical product or liquid during the method for the aseptic filling of bags with said pharmaceutical product or liquid.

In a preferred embodiment, the pharmaceutical product or liquid is a liquid of biological origin, more preferably, blood or products derived from blood such as plasma, serum, red blood cell solution, albumin solution, α1-antitrypsin solution, von Willebrand factor solution, solution comprising coagulation factors such as factor VII, factor VIII and factor IX, immunoglobulin solution, plasminogen solution, plasmin solution, antithrombin III solution, fibrinogen solution, fibrin solution, thrombin solution or combinations thereof. It is also envisaged that the pharmaceutical product or liquid is not of biological origin but is obtained by any other process or method known in the prior art, such as chemical synthesis, recombinant production or transgenic production. Therefore in another preferred embodiment the proteins of the solutions of albumin, α1-antitrypsin, von Willebrand factor, coagulation factors such as factor VII, factor VIII and factor IX, immunoglobulins, plasminogen solution, plasmin solution, antithrombin III solution, fibrinogen solution, fibrin solution, thrombin solution or combinations thereof can be obtained by chemical synthesis, by recombinant production or by transgenic production thereof by any of the methods known in the prior art. In the most preferred embodiment, the pharmaceutical product or liquid is an albumin solution of biological origin, produced by chemical synthesis or obtained by recombinant or transgenic production, preferably of biological origin.

In addition, the present invention discloses the use of the method of the present invention to prevent contamination of a pharmaceutical product or liquid during the method for the aseptic filling of bags with said pharmaceutical product or liquid. In a more preferred embodiment, said use allows to prevent the biological contamination and/or contamination by particles resulting from the welding process, during the method for the aseptic filling of bags with said pharmaceutical product or liquid.

In a preferred embodiment, the pharmaceutical product or liquid is a liquid of biological origin, more preferably, blood or products derived from blood such as plasma, serum, red blood cell solution, albumin solution, α1-antitrypsin solution, von Willebrand factor solution, solution comprising coagulation factors such as factor VII, factor VIII and factor IX, immunoglobulin solution, plasminogen solution, plasmin solution, antithrombin III solution, fibrinogen solution, fibrin solution, thrombin solution or combinations thereof. It is also envisaged that the pharmaceutical product or liquid is not of biological origin but is obtained by any other process or method known in the prior art, such as chemical synthesis, recombinant production or transgenic production. Therefore in another preferred embodiment the proteins of the solutions of albumin, α1-antitrypsin, von Willebrand factor, coagulation factors such as factor VII, factor VIII and factor IX, immunoglobulins, plasminogen solution, plasmin solution, antithrombin III solution, fibrinogen solution, fibrin solution, thrombin solution or combinations thereof can be obtained by chemical synthesis, by recombinant production or by transgenic production thereof by any of the methods known in the prior art. In the most preferred embodiment, the pharmaceutical product or liquid is an albumin solution of biological origin, produced by chemical synthesis or obtained by recombinant or transgenic production, preferably of biological origin.

As mentioned earlier, the present invention also discloses a bag comprising a pharmaceutical product or liquid filled by any of the methods of the present invention.

In a preferred embodiment, the pharmaceutical product or liquid is a liquid of biological origin, more preferably, blood or products derived from blood such as plasma, serum, red blood cell solution, albumin solution, α1-antitrypsin solution, von Willebrand factor solution, solution comprising coagulation factors such as factor VII, factor VIII and factor IX, immunoglobulin solution, plasminogen solution, plasmin solution, antithrombin III solution, fibrinogen solution, fibrin solution, thrombin solution or combinations thereof. It is also envisaged that the pharmaceutical product or liquid is not of biological origin but is obtained by any other process or method known in the prior art, such as chemical synthesis, recombinant production or transgenic production. Therefore in another preferred embodiment the proteins of the solutions of albumin, α1-antitrypsin, von Willebrand factor, coagulation factors such as factor VII, factor VIII and factor IX, immunoglobulins, plasminogen solution, plasmin solution, antithrombin III solution, fibrinogen solution, fibrin solution, thrombin solution or combinations thereof can be obtained by chemical synthesis, by recombinant production or by transgenic production thereof by any of the methods known in the prior art. In the most preferred embodiment, the pharmaceutical product or liquid is an albumin solution of biological origin, produced by chemical synthesis or obtained by recombinant or transgenic production, preferably of biological origin.

In said bag filled with a pharmaceutical product or liquid produced by any of the methods of the present invention, the at least one inlet/cap structure has the characteristics mentioned and explained in detail above. The characteristics of the bag are also explained and detailed above.

The main advantage of the method of the present invention is that it allows preventing external particles or particles resulting from the welding process from entering into the bag during the method for filling said bag with a pharmaceutical product or liquid.

Another additional advantage of the method of the present invention is that biological contamination is also prevented by maintaining the sterility of the inside of the bag at all times using different methods (for example, using an inlet/cap structure and carrying out different steps of the method in a horizontal laminar flow).

Moreover, the method allows minimising the time and area of exposure to ultrasounds and/or heat during the welding process, minimising or eliminating the related exposure of the pharmaceutical product or liquid contained in the bag. An additional advantage of the method of the present invention is therefore that it succeeds in minimising or eliminating the risk of the colour and/or biological properties and biological activity of the pharmaceutical product or liquid introduced into the bag being affected or altered.

Finally, as explained earlier, an additional advantage of the present invention is that providing an inlet/cap structure with two closure positions, one of them being a reversible hermetic closure, allows separation in time and space to be provided between some of the steps of the method of the present invention, that is, it makes it possible to pause or stop the process for given periods of time at various points thereof and for the different steps forming the method of the present invention to be carried out at the same location, space or room or in different locations, spaces or rooms.

For a better understanding, the present invention is described below with reference to the accompanying drawings, which are given as an example and which can in no circumstances limit the present invention. Equivalent or similar structures in different figures are indicated with the same numeral.

Figure 17:
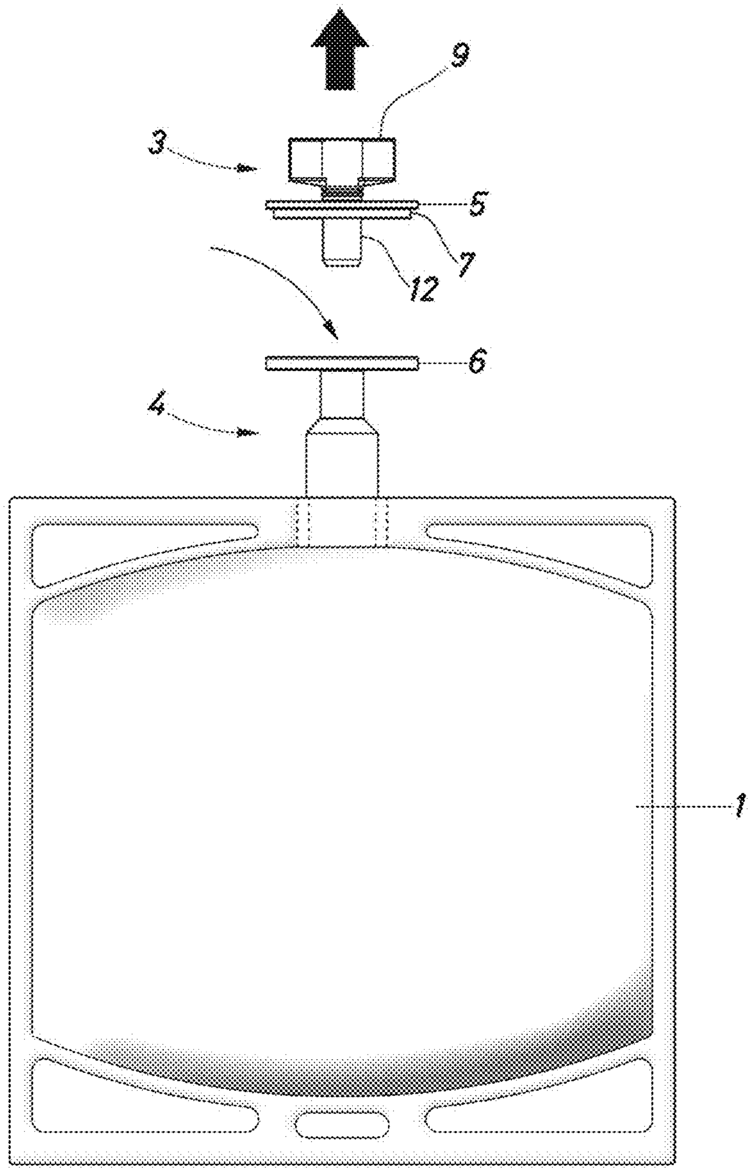

FIG. 17 is a diagrammatic view of the second step (step b)) of the method for the aseptic filling of a bag with a pharmaceutical product or liquid of the present invention, according to the first embodiment of the conjunction between the lower surface of the cap flange and the upper surface of the inlet flange, that is, according to the inlet/cap structure shown in FIGS. 2 to 8. In this figure, the narrow arrow which has no numeral denotes or represents the action of filling the bag with the pharmaceutical product or liquid carried out in the second step (step b)) of the method of the present invention.

Figure 18:
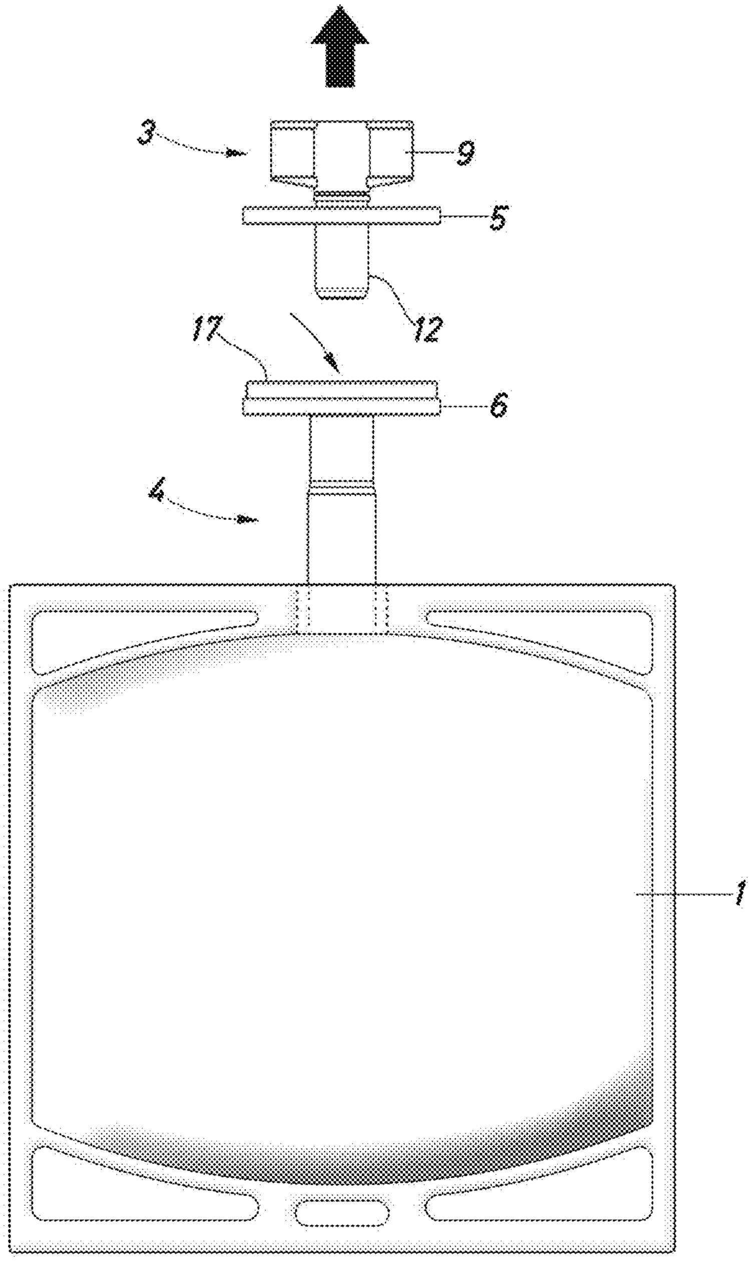

FIG. 18 is a diagrammatic view of the second step (step b)) of the method for the aseptic filling of a bag with a pharmaceutical product or liquid of the present invention, according to the second embodiment of the conjunction between the lower surface of the cap flange and the upper surface of the inlet flange, that is, according to the inlet/cap structure shown in FIGS. 9 to 15. In this figure, the narrow arrow with no numeral denotes or represents the action of filling the bag with the pharmaceutical product or liquid carried out in the second step (step b)) of the method of the present invention.

Figure 19:
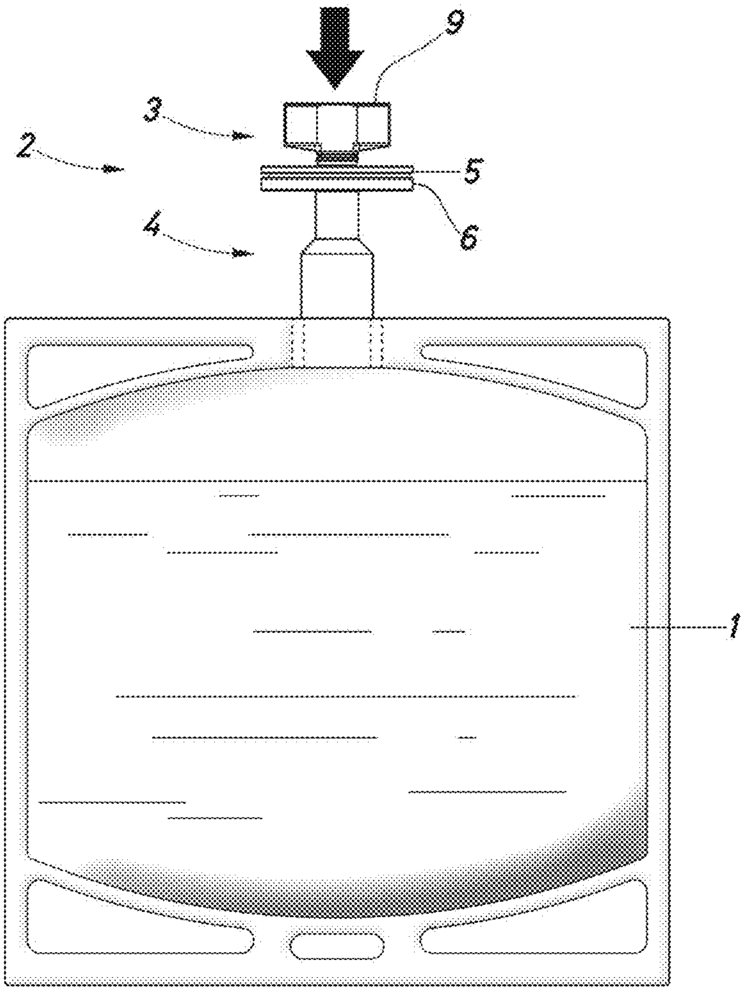

FIG. 19 is a diagrammatic view of the third step (step c)) of the method for the aseptic filling of a bag with a pharmaceutical product or liquid of the present invention in which it can be seen that the cap has been newly inserted in the inlet of the bag and that said bag already contains the pharmaceutical product or liquid. This diagrammatic view may relate to any of the embodiments which will be explained in greater detail below and which are shown in the rest of the figures.

Figure 20:
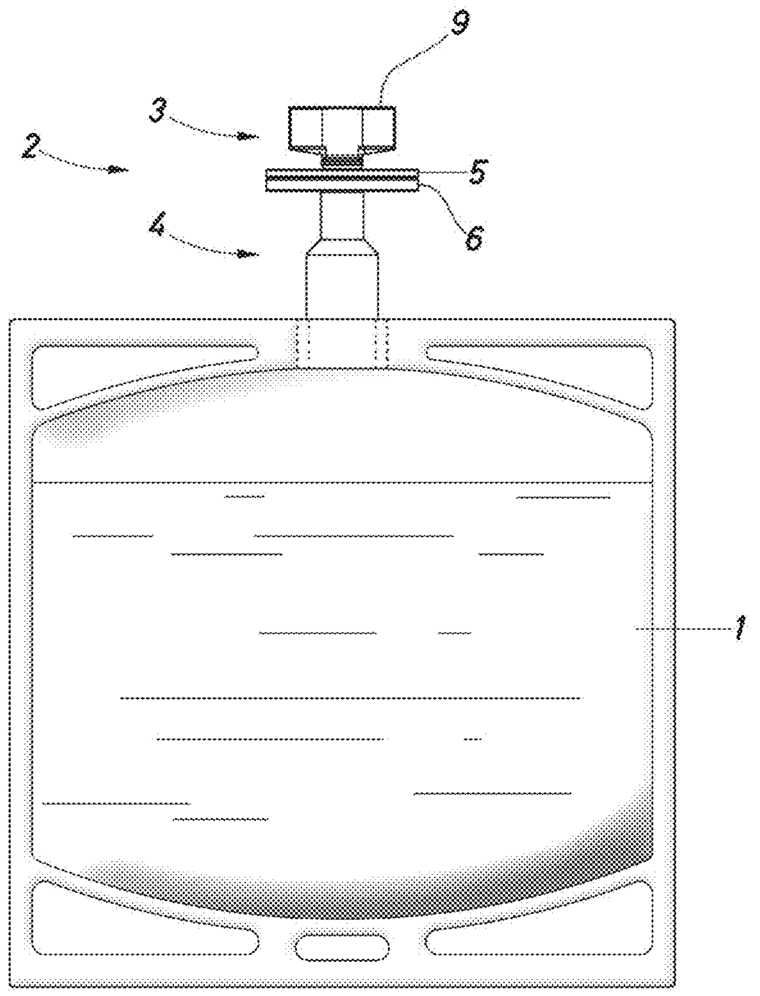

FIG. 20 is a diagrammatic view of the fourth step (step d)) of the method for the aseptic filling of a bag with a pharmaceutical product or liquid of the present invention. This diagrammatic view may relate to any of the embodiments which will be explained in more detail below and are show in the rest of the figures.

Figure 21:
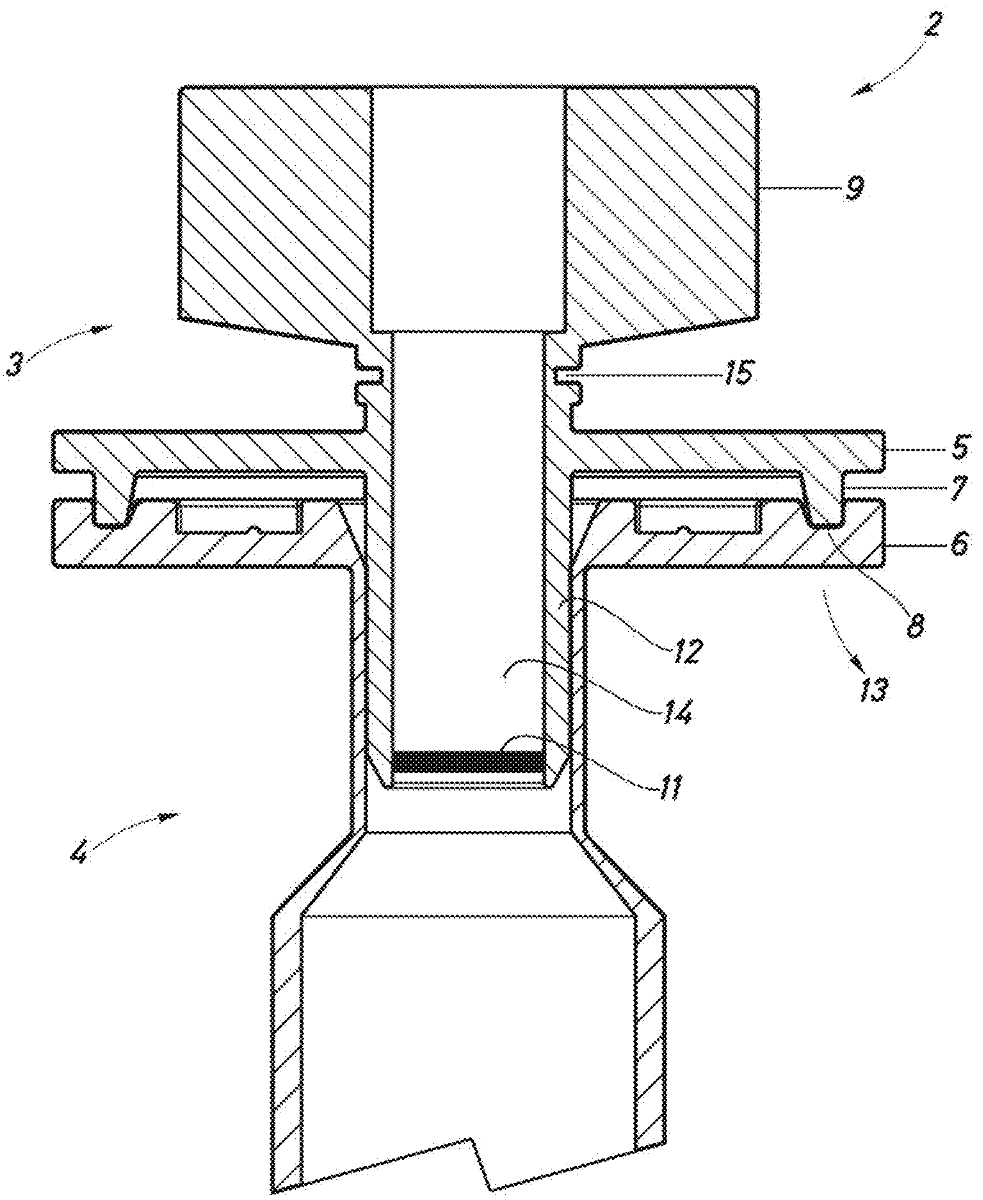

FIG. 21 is a cross section or transverse section of a view in detail of the inlet/cap structure seen in the first and third steps of the method of the present invention (steps a) and c)). Said inlet/cap structure is according to the first embodiment, that is, according to the inlet/cap structure shown in FIGS. 2 to 8.

Figure 22:
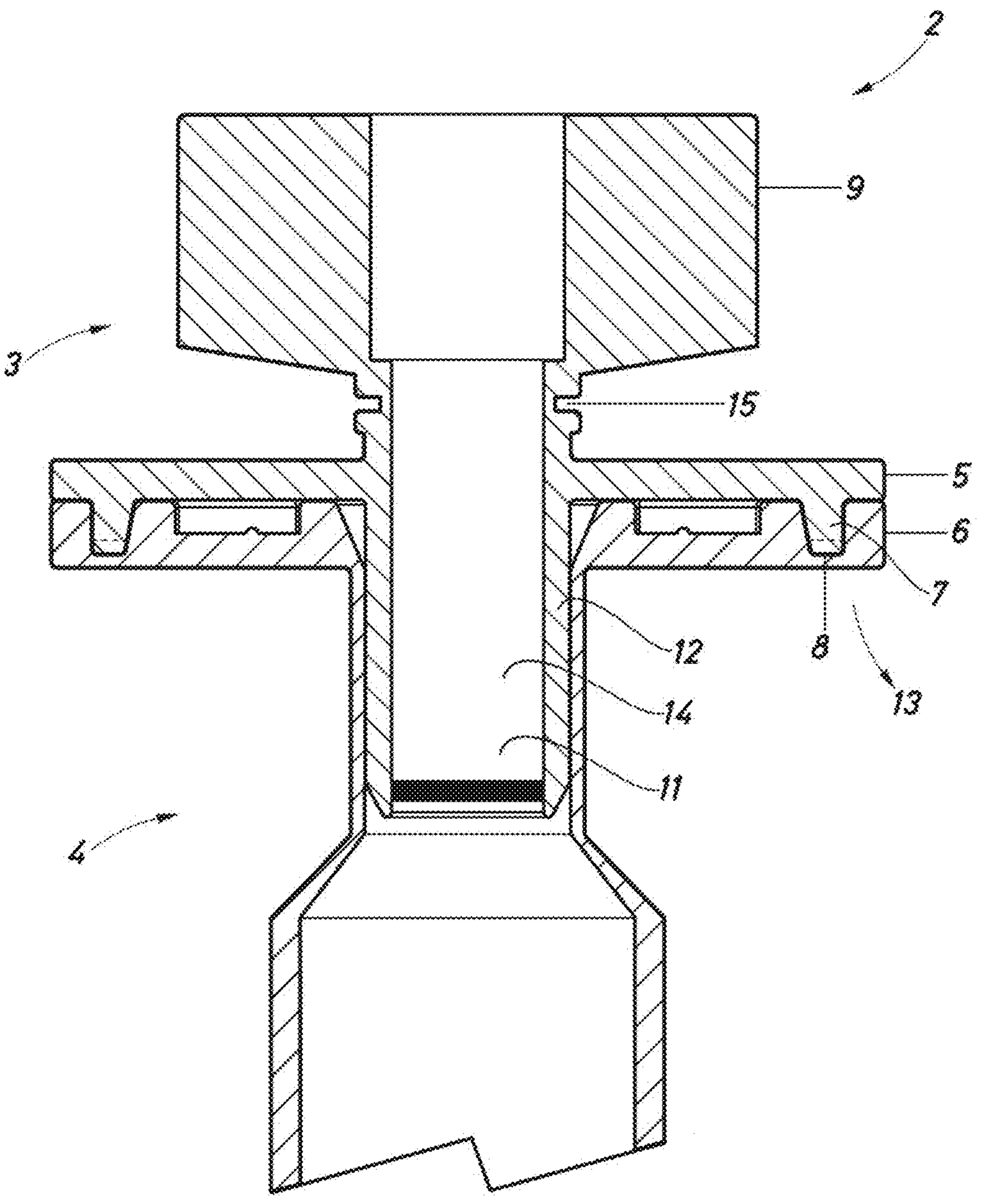

FIG. 22 is a cross section or transverse section of a view in detail of the inlet/cap structure seen in the fourth step of the method of the present invention (step d)). Said inlet/cap structure is according to the first embodiment, that is, according to the inlet/cap structure shown in FIGS. 2 to 8.

Figure 23:
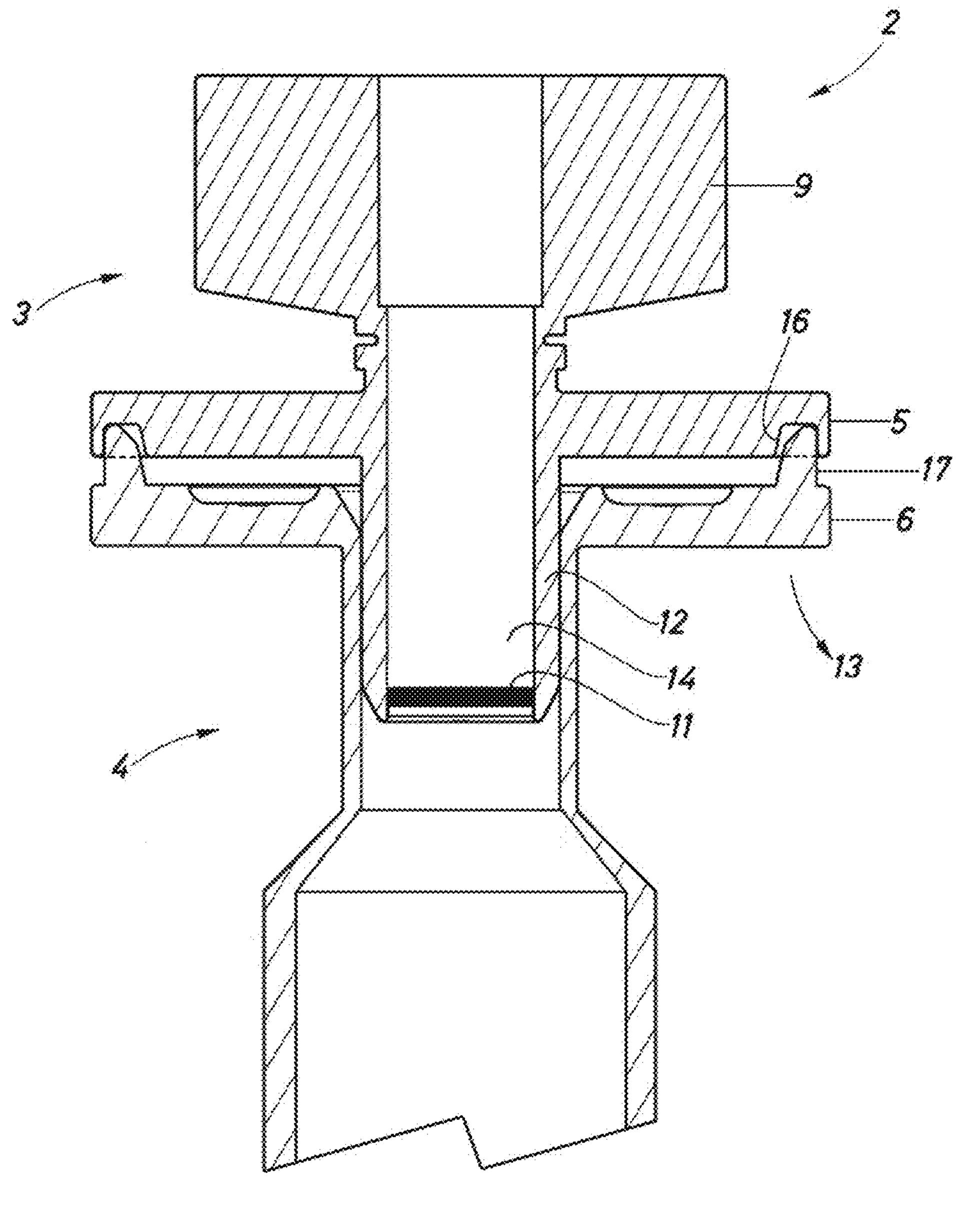

FIG. 23 is a cross section or transverse section of a view in detail of the inlet/cap structure seen in the first and third steps of the method of the present invention (steps a) and c)). Said inlet/cap structure is according to the second embodiment, that is, according to the inlet/cap structure shown in FIGS. 9 to 15.

Figure 24:
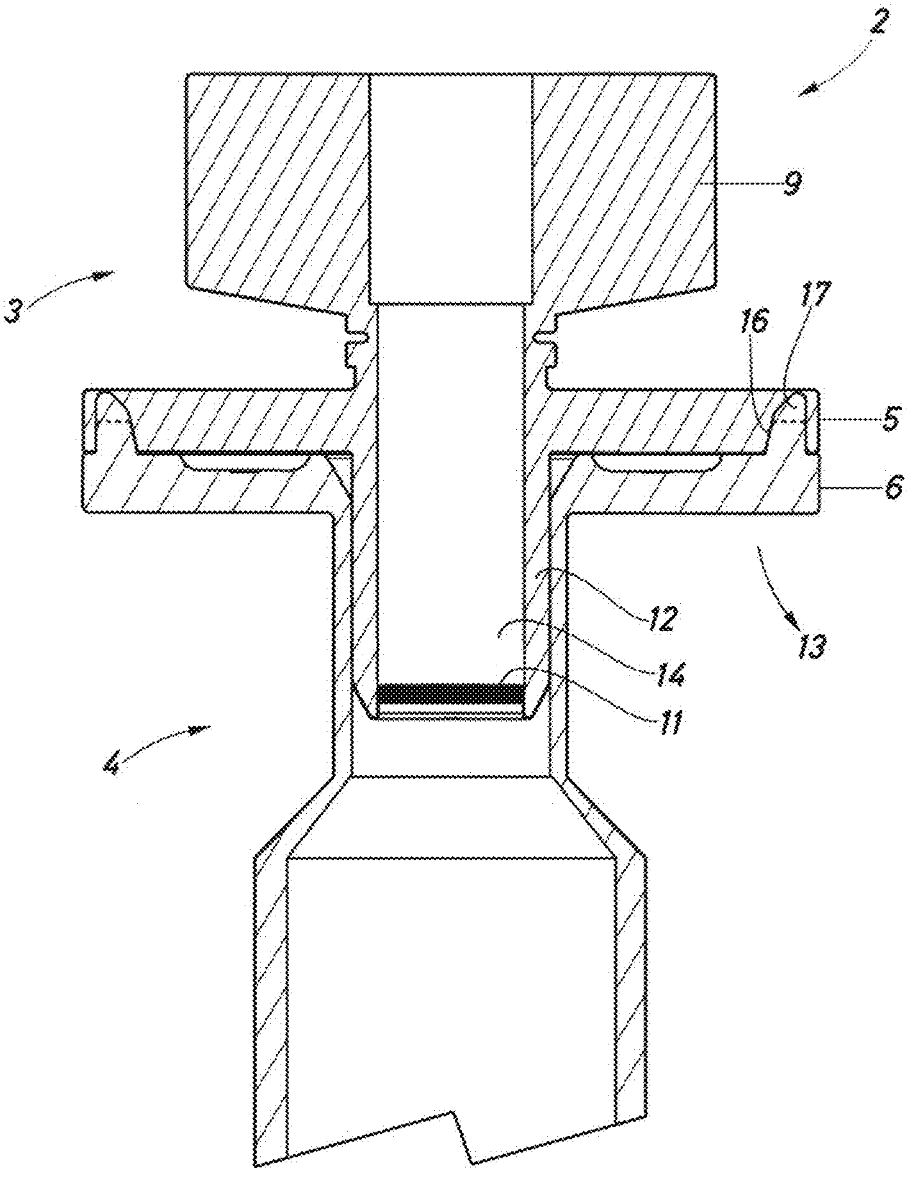

FIG. 24 is a cross section or transverse section of a view in detail of the inlet/cap structure seen in the fourth step of the method of the present invention (step d)). Said inlet/cap structure is according to the second embodiment, that is, according to the inlet/cap structure shown in FIGS. 9 to 15.

Figure 1:
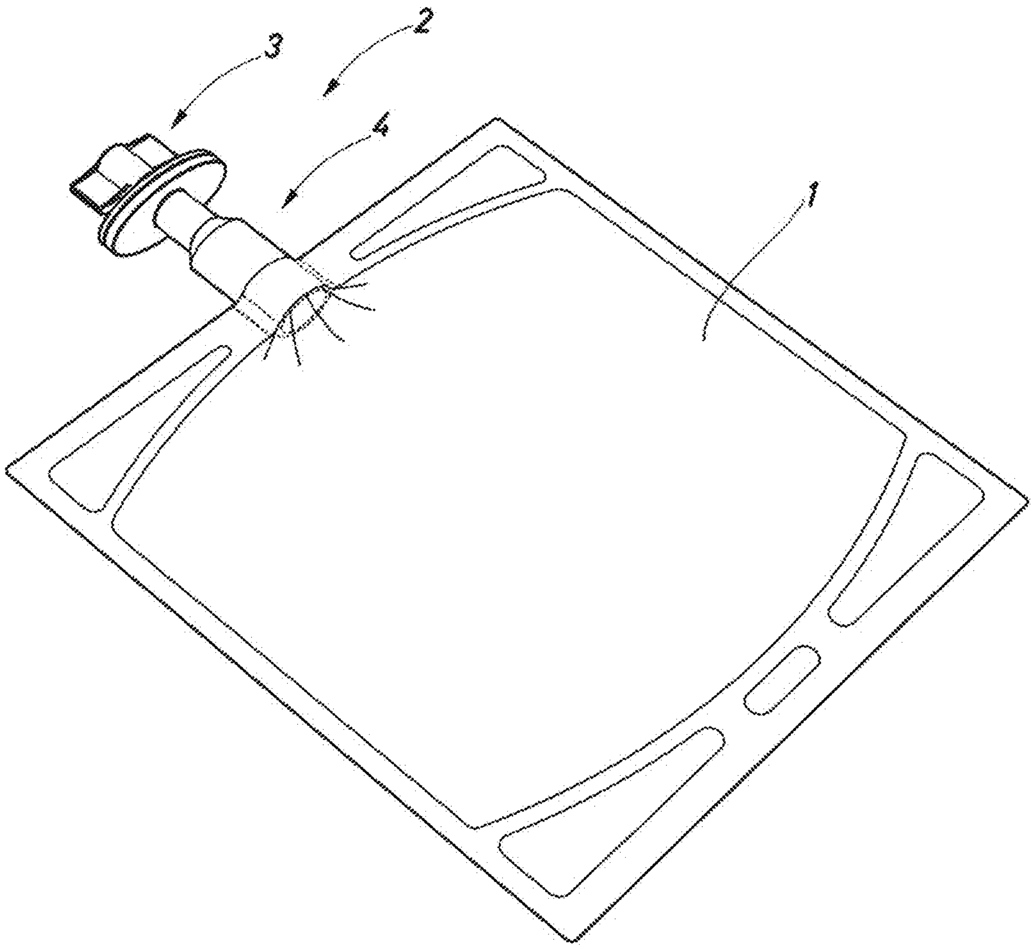
FIG. 1 is a perspective view of an empty bag with the inlet/cap structure of the present invention required to implement the method for the aseptic filling of bags with a pharmaceutical product or liquid of the present invention. Said perspective view may relate to any of the embodiments which will be explained in more detail below and which are shown in the rest of the figures.

FIG. 1, as explained earlier, is a perspective view of a bag with the inlet/cap structure of the present invention which may correspond to any of the embodiments which will be explained in more detail below and which appear in rest of the figures. Said FIG. 1 shows a bag -1- for use in the method of the present invention. Said bag -1- comprises an inlet/cap structure -2- formed by a cap -3- and an inlet -4-. Specifically, FIG. 1 shows an embodiment in which said cap -3- is inserted or fixed in said inlet -4- producing a hermetic closure and thus would or could correspond to the first step (step a)) of the method of the present invention.

With regard to the inlet/cap structure -2- shown in said FIG. 1, the two most preferred embodiments thereof are explained below, which are differentiated by the conjunction between the lower surface of the flange -5- of the cap -3- and the upper surface of the flange -6- of the inlet -4-.

In the first of said embodiments, which is shown in FIGS. 2 to 8, the conjunction between the inlet -4- and the cap -3- is produced by means of a crown -7- present on the flange -5- of said cap -3- and a recess -8- present on the flange -6- of said inlet -4-.

Figure 2:
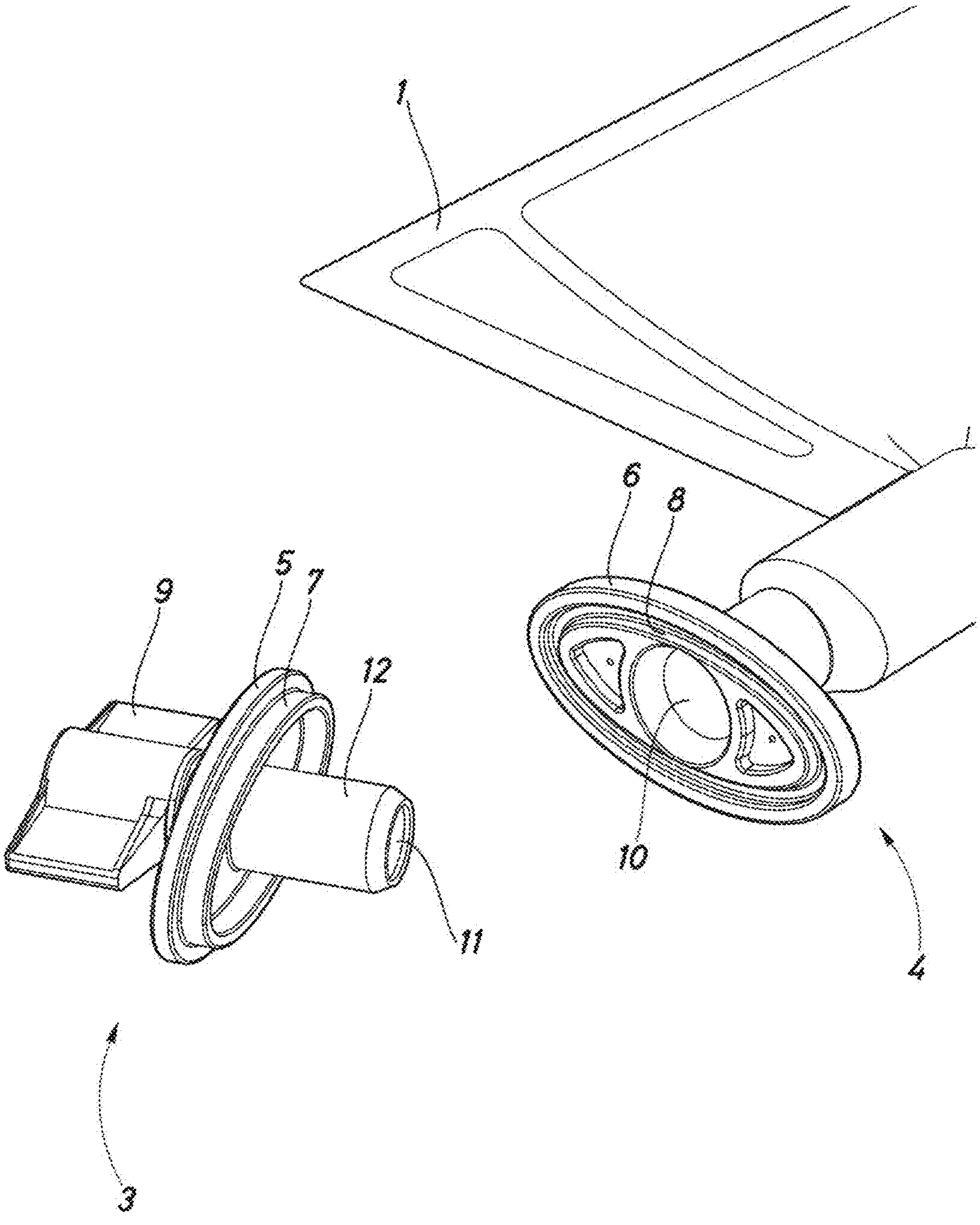
FIG. 2 is a perspective view of a detail of the cap and the inlet of the bag shown in FIG. 1 separated and according to a first embodiment of the conjunction between the lower surface of the cap flange and the upper surface of the inlet flange.

The inlet/cap structure present on the bag -1- and shown in FIG. 1 can be seen in detail in FIG. 2, according to the first embodiment of said inlet/cap structure. In this case, the cap -3- has been represented separated from the inlet -4-, so that the structure of the contact surfaces of the flanges -5- and -6- can be seen. As can be seen, the cap -3- has an actuation key -9- in the upper portion thereof which normally has a weakened zone in the contact thereof with the rest of the cap structure and, thus, can be removed or actuated by the user by a mechanical action (rotation thereof, for example) when the bag is to be used. Contiguous with said key -9-, the cap -3- comprises an oval-shaped flange -5- which extends in a crown -7- of smaller diameter, which is also oval, (that is, with a continuous projection on the lower surface thereof which runs round said lower surface at the periphery thereof describing the same oval shape as the flange -5-). The flange -5- has a distal cylindrical extension -12- which in turn has a membrane -11- at the end thereof.

The inlet -4- in turn has an oval-shaped flange -6- which has an upper surface with a continuous recess -8- which runs round the periphery thereof describing the same oval shape as the flange -6-. There may be additional structures in said upper surface of the flange -6-, for example the two semi-elliptical recesses that can be seen in FIG. 2. Said additional structures respond to various design needs, for example, to save and optimise material. Finally, the channel -10- of the inlet -4- can be seen in the centre of the flange -6-.

Figure 3:
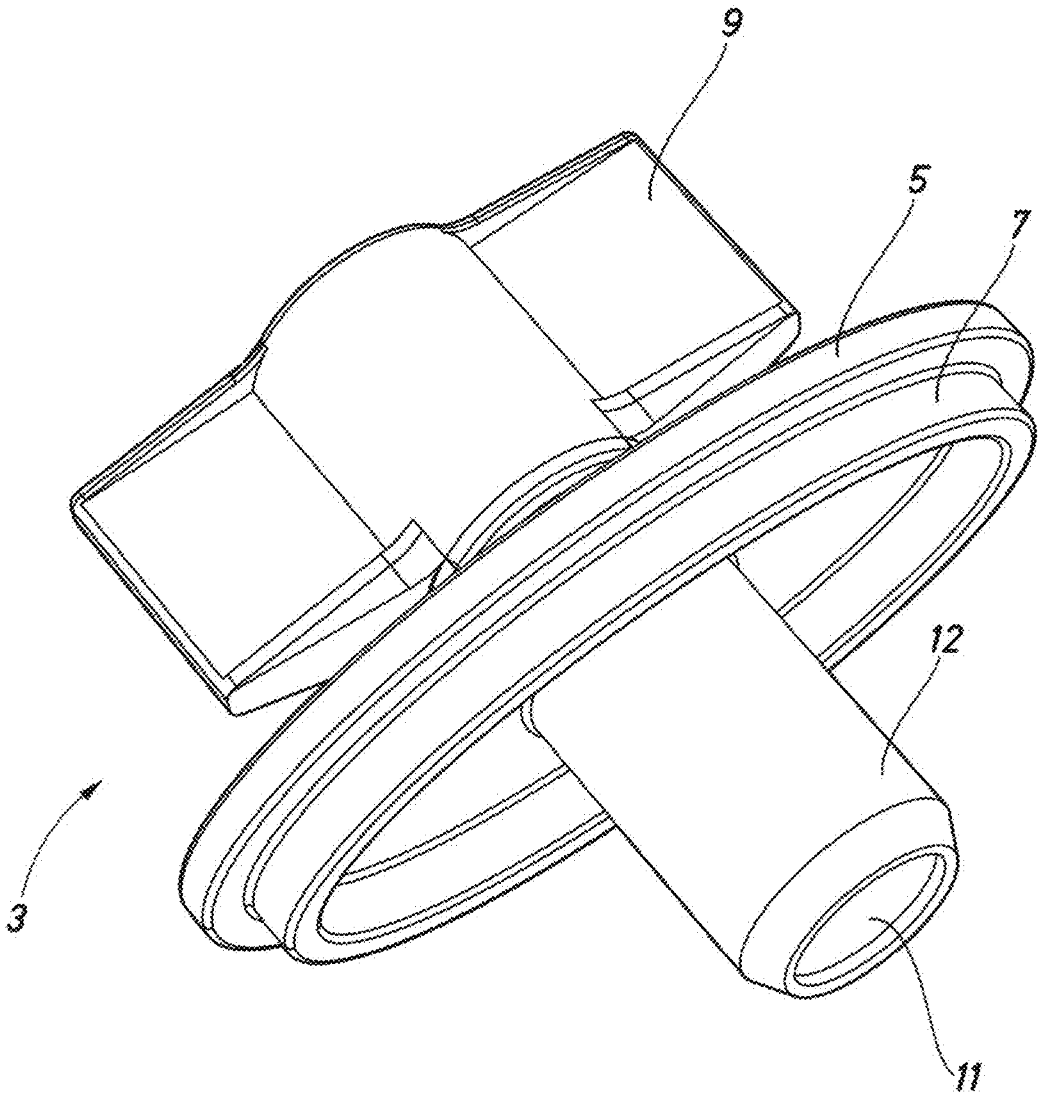
FIG. 3 is a perspective view of a detail of the cap shown in FIGS. 1 and 2 according to a first embodiment of the conjunction between the lower surface of the cap flange and the upper surface of the inlet flange.
Figure 4:
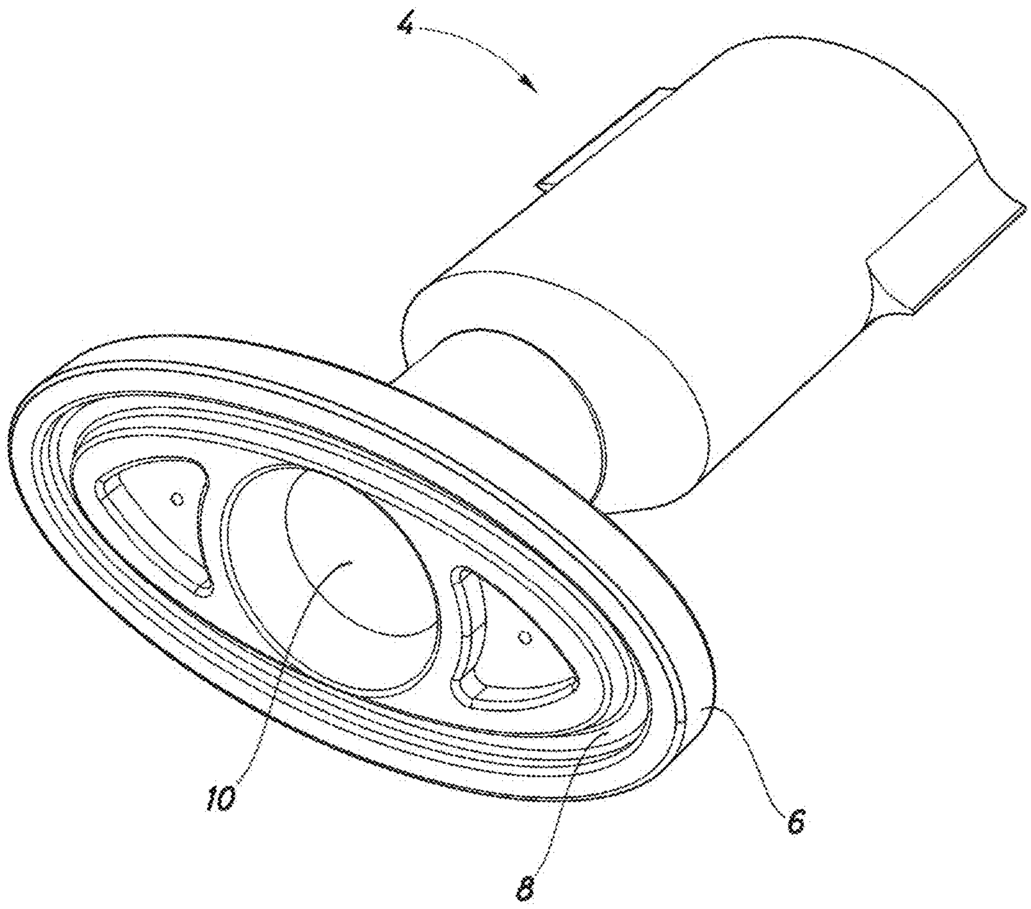
FIG. 4 is a perspective view of a detail of the inlet shown in FIGS. 1 and 2 according to a first embodiment of the conjunction between the lower surface of the cap flange and the upper surface of the inlet flange.

FIGS. 3 and 4 show the cap -3- and the inlet -4-, respectively, in detail. The structural details that can be seen or distinguished in said figures are the same as can be seen in FIG. 2. Thus the cap -3- in FIG. 3 has an actuation key -9- in the upper portion thereof which normally can be removed or actuated by the user by mechanical action (rotation, for example) when the bag is to be used. Contiguous with said key -9-, the cap -3- comprises an oval-shaped flange -5- which extends in a crown -7- of smaller diameter and also oval (that is, the lower surface thereof has a continuous projection which runs round said lower surface at the periphery thereof describing the same oval shape as the flange -5-). The flange -5- has a distal cylindrical extension -12- which in turn has a membrane -11- at the end thereof. In FIG. 4, the inlet -4- has an oval-shaped flange -6- which has an upper surface with a continuous recess -8- which runs round said upper surface at the periphery thereof describing the same oval shape as the flange -6-. There may be additional structures on said upper surface of the flange -6-, such as the two semi-elliptical recesses that can be seen in FIG. 4 (positioned between the recess -8- and the channel -10-). Said additional structures respond to various design needs, for example, to save or optimise materials. Finally, the channel -10- of the inlet -4- can be seen in the centre of the flange -6-.

Figure 5:
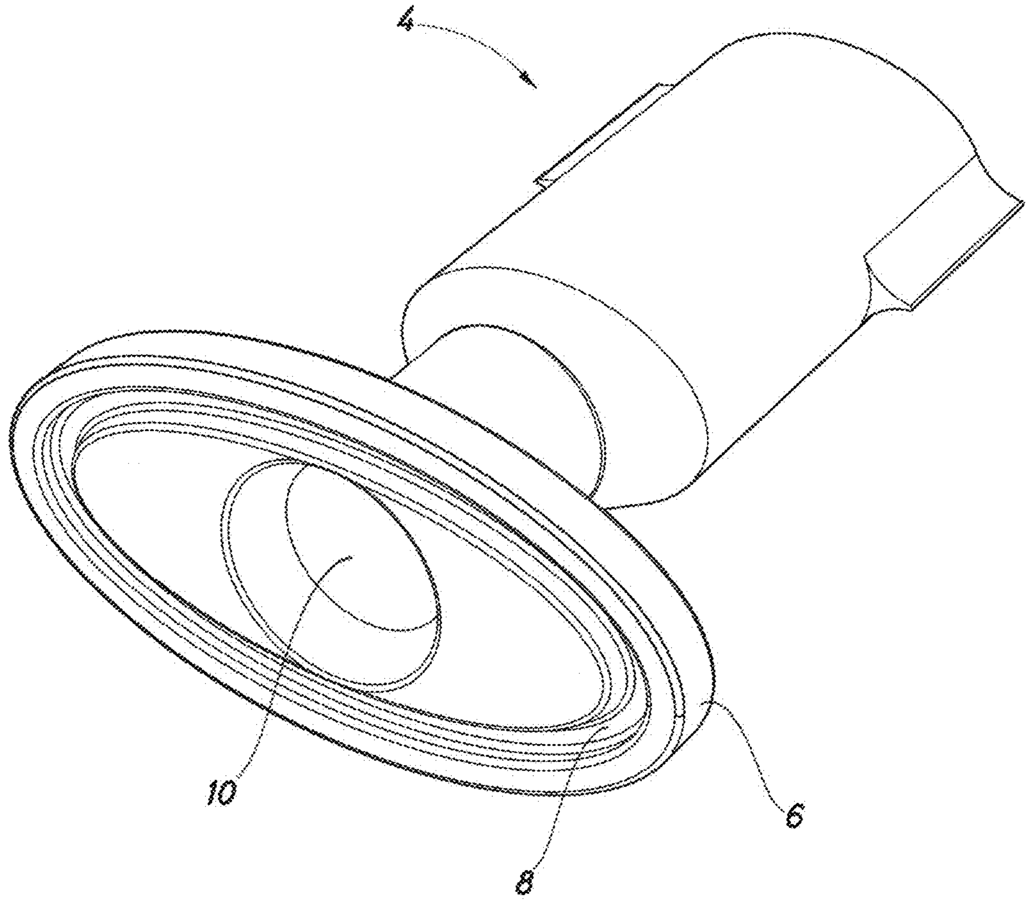
FIG. 5 is a perspective view of a detail of an alternative embodiment of the inlet shown in FIG. 4.

FIG. 5 shows an alternative embodiment of the inlet -4- of FIG. 4, in which the upper surface of the flange -6- does not have the two semi-elliptical recesses but instead said upper surface is completely conjoined with the lower surface of the flange -5- shown in FIGS. 2 and 3 for the cap -3-. As in FIG. 4, the inlet -4- has a continuous recess -8- on the upper surface of the oval flange -6- which runs round said upper surface at the periphery thereof describing the same oval shape as the flange -6-; and the channel -10- of said inlet can be seen in the centre of the flange -6-.

Figure 6:
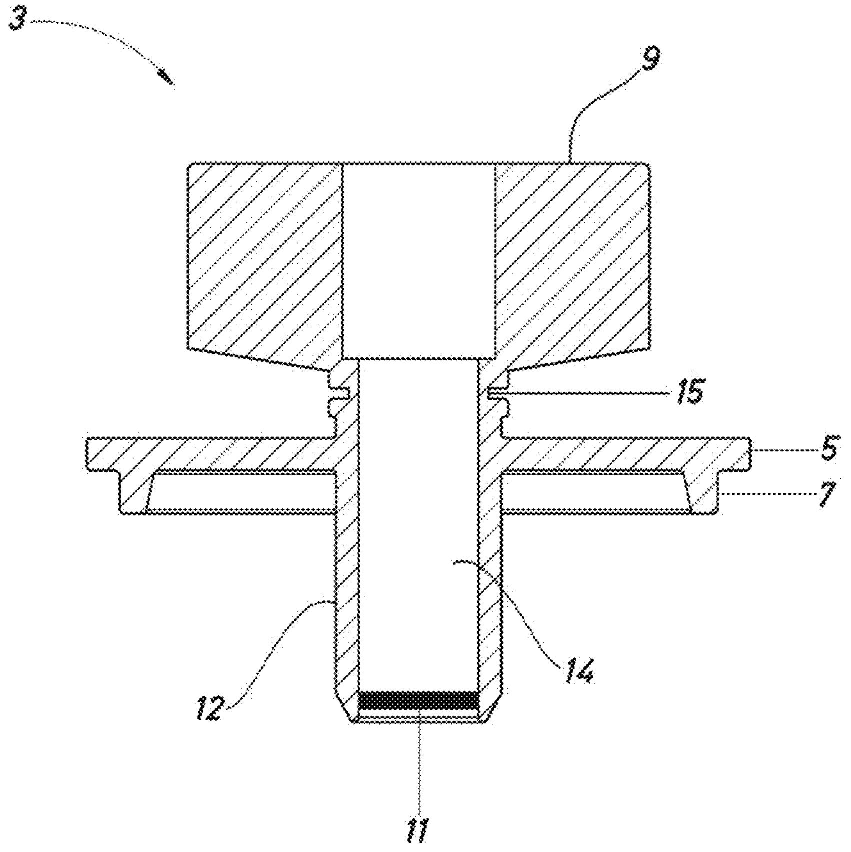
FIG. 6 is a cross section or central transverse section of the cap shown in FIG. 3 in a plane that passes through the semi-major axis of the ellipse described by the flange of said cap.

The cross section or central transverse section of the cap -3- shown in FIG. 3 can be seen in FIG. 6. It can be seen in this FIG. 6 that said cap comprises a central cylindrical zone formed by the channel -14- inside the distal cylindrical extension -12- which allows the hermetic closure to be produced between the inlet and the cap. In the upper portion of said cylindrical structure the actuation key -9- is positioned which can be removed by the user by mechanical action (rotation thereof, for example) as mentioned earlier. Said key -9- is connected to said distal cylindrical extension -12- by means of a weakened zone -15-, that is, a zone where the amount of material in the wall is less and therefore allows easy rotation thereof. As can be seen in FIG. 6, the channel -14- extends inside the key -9- but has a larger diameter. Below said key -9-, after said weakened zone -15-, the flange -5- is situated which extends in a crown -7- of smaller diameter and also oval. Finally, at the end of the distal cylindrical extension -12-, there is a membrane -11-.

Figure 7:
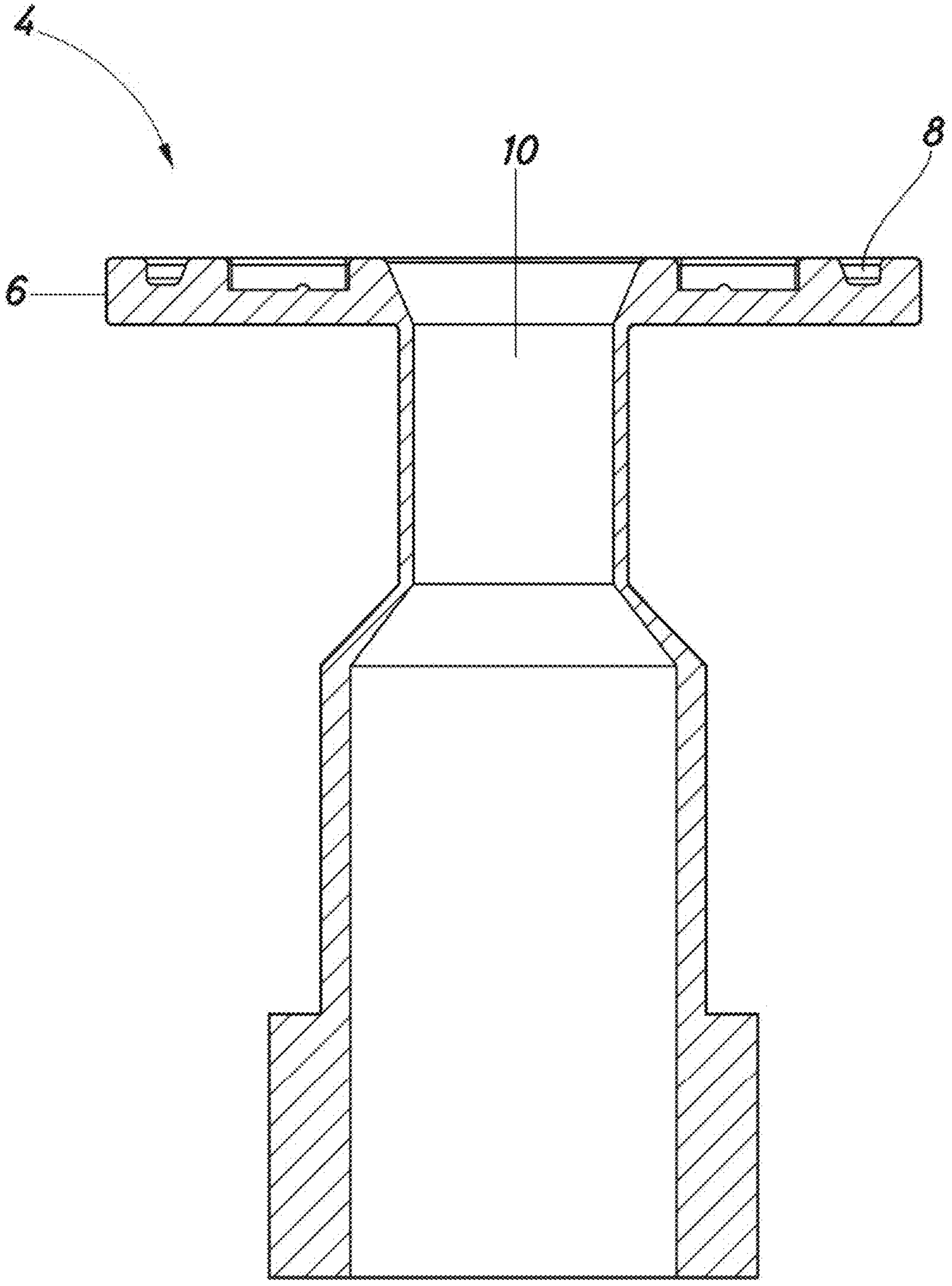
FIG. 7 is a cross section or central transverse section of the inlet shown in FIG. 4 in a plane that passes through the semi-major axis of the ellipse described by the flange of said inlet.

FIG. 7 shows a cross section or central transverse section of the inlet -4- shown in FIG. 4 and the same structures or details as in said FIG. 4 can therefore be seen. In FIG. 7 it can be seen that the flange -6- of the inlet -4- has on the upper surface thereof a continuous recess -8- which runs round said upper surface at the periphery thereof describing the same oval shape as the flange -6-. As mentioned for FIG. 4, there may be additional structures on said upper surface of the flange -6-, for example, the two recesses located between the recess -8- and the channel -10-. Said additional structures respond to various design needs, for example, saving or optimising materials. Finally, the channel -10- of the inlet -4- can be seen in the centre of the flange -6-.

Figure 8:
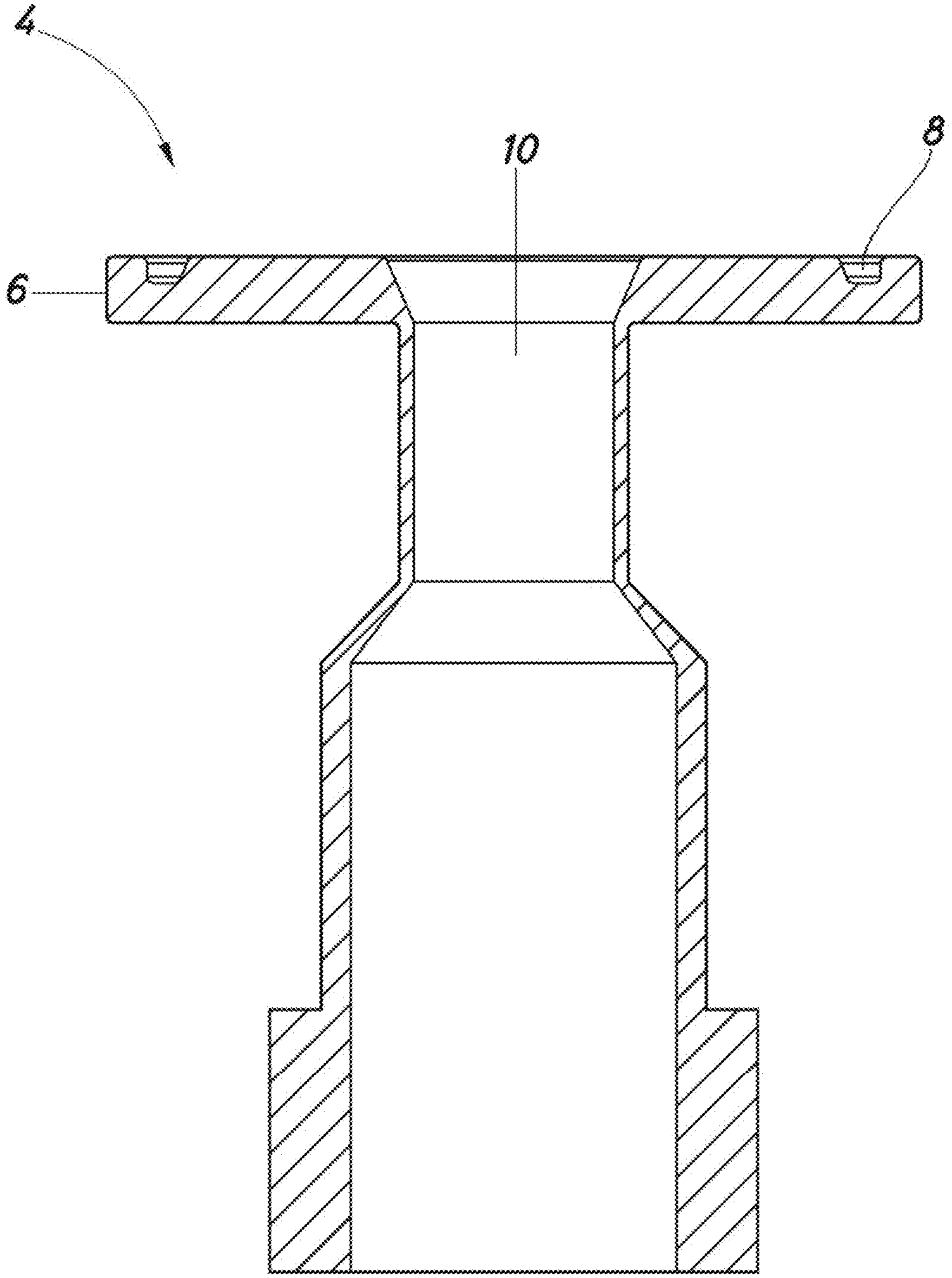
FIG. 8 is a cross section or central transverse section of the inlet shown in FIG. 5 in a plane that passes through the semi-major axis of the ellipse described by the flange of said inlet.

FIG. 8 shows a cross section or central transverse section of the inlet -4- shown in FIG. 5, that is, an alternative embodiment of the inlet compared with that shown in FIG. 7. As in the case of FIGS. 4 and 5, the only difference between FIGS. 7 and 8 is that the inlet -4- shown in FIG. 8 does not have the two recesses located between the channel -10 and the recess -8- on the flange -6-. The upper surface of the flange -6- shown in FIG. 8 is therefore completely conjoined with the lower surface of the flange -5- shown in FIG. 6.

In the second of the embodiments mentioned above, which is shown in FIGS. 9 to 15, the conjunction between the inlet -4- and the cap -3- is produced by means of a recess -16- present on the flange -5- of said cap -3- and a crown -17- present on the flange -6- of said inlet -4-.

Figure 9:
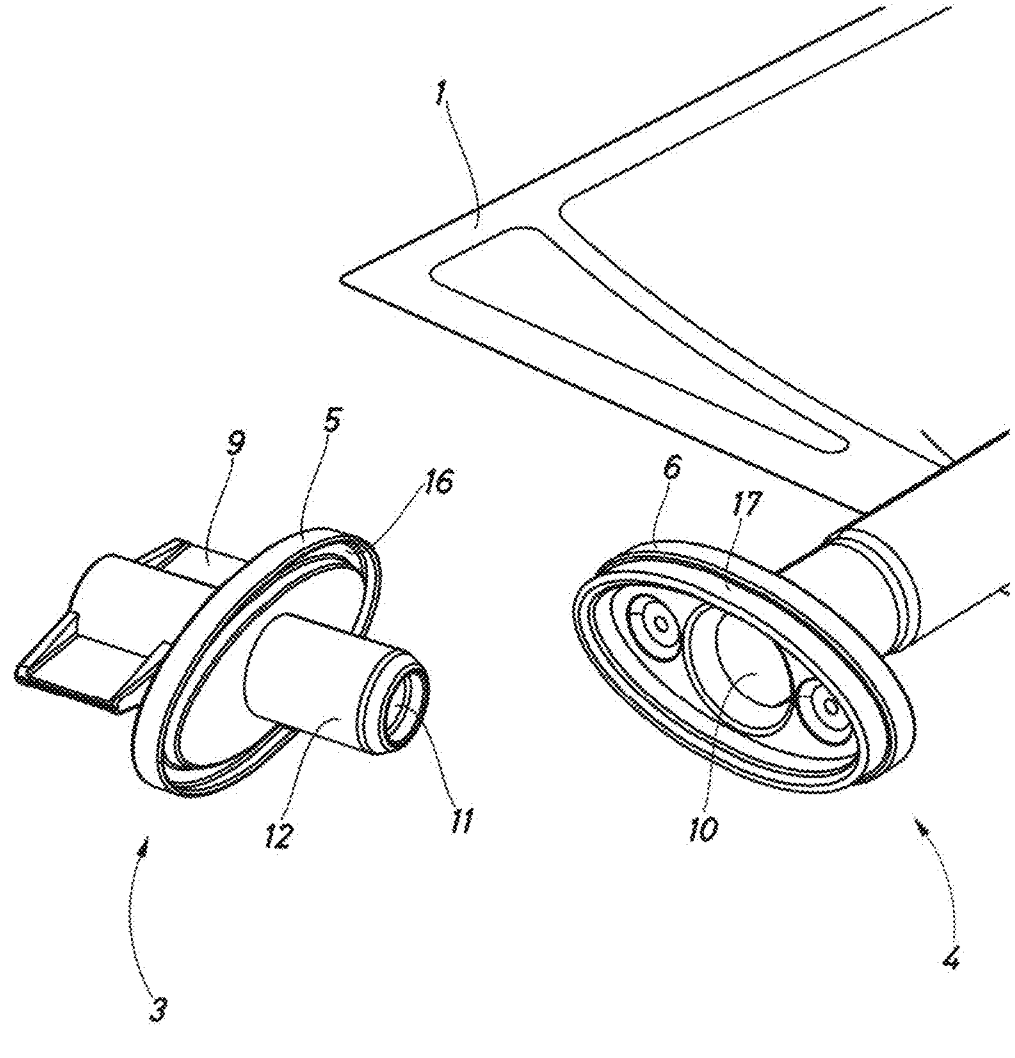
FIG. 9 is a perspective view of a detail of the cap and the inlet of the bag shown in FIG. 1 separated and according to a second embodiment of the conjunction between the lower surface of the cap flange and the upper surface of the inlet flange.

FIG. 9 shows in detail the inlet/cap structure present on the bag -1- and shown in FIG. 1, according to the second embodiment of said inlet/cap structure. In this case, the cap -3- has been represented separated from the inlet -4-, so as to show the structure of the contact surfaces of the flanges -5- and -6-. As can be seen, the cap -3- has an actuation key -9- in the upper portion thereof, which normally has a weakened zone in the contact thereof with the rest of the cap structure and can therefore be removed or actuated by the user by mechanical action (rotation thereof, for example) when the bag is to be used. Contiguous with said key -9-, the cap -3- comprises an oval-shaped flange -5- which has a lower surface with a continuous recess -16- which runs round said lower surface at the periphery thereof describing the same oval shape as the flange -5-. The flange -5- has a distal cylindrical extension -12- which in turn has a membrane -11- at the end thereof.

The inlet -4- in turn has an oval-shaped flange -6- which extends in a crown -17- of smaller diameter but also oval (that is, on the upper surface thereof, the flange -6- of the inlet -4- has a continuous projection which runs round said upper surface at the periphery thereof describing the same oval shape as the flange -6-). On said upper surface of the flange -6- there may be additional structures, for example the two circular recesses that can be seen in FIG. 9 (located between the crown -17- and the channel -10-). Said additional structures respond to various design needs, for example saving or optimising materials. Finally, the channel -10- of the inlet -4- can be seen in the centre of the flange -6-.

Figure 10:
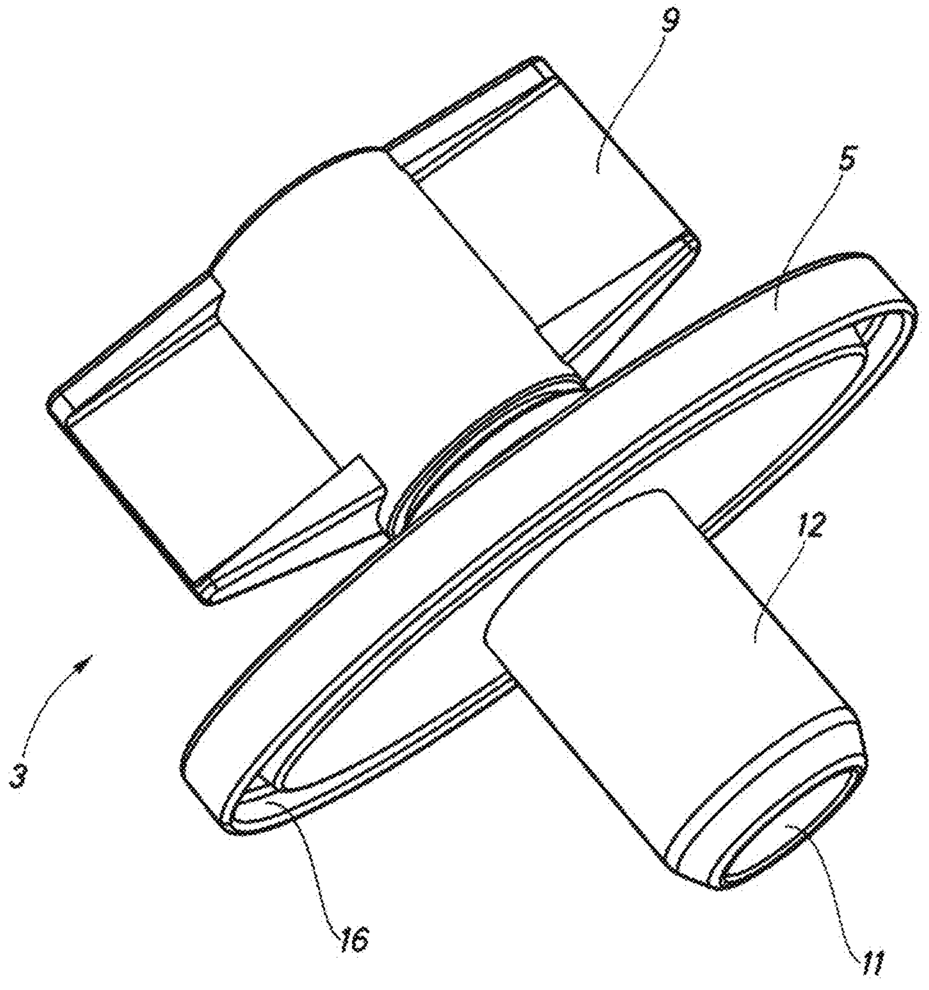
FIG. 10 is a perspective view of a detail of the cap shown in FIGS. 1 and 9 according to a second embodiment of the conjunction between the lower surface of the cap flange and the upper surface of the inlet flange.
Figure 11:
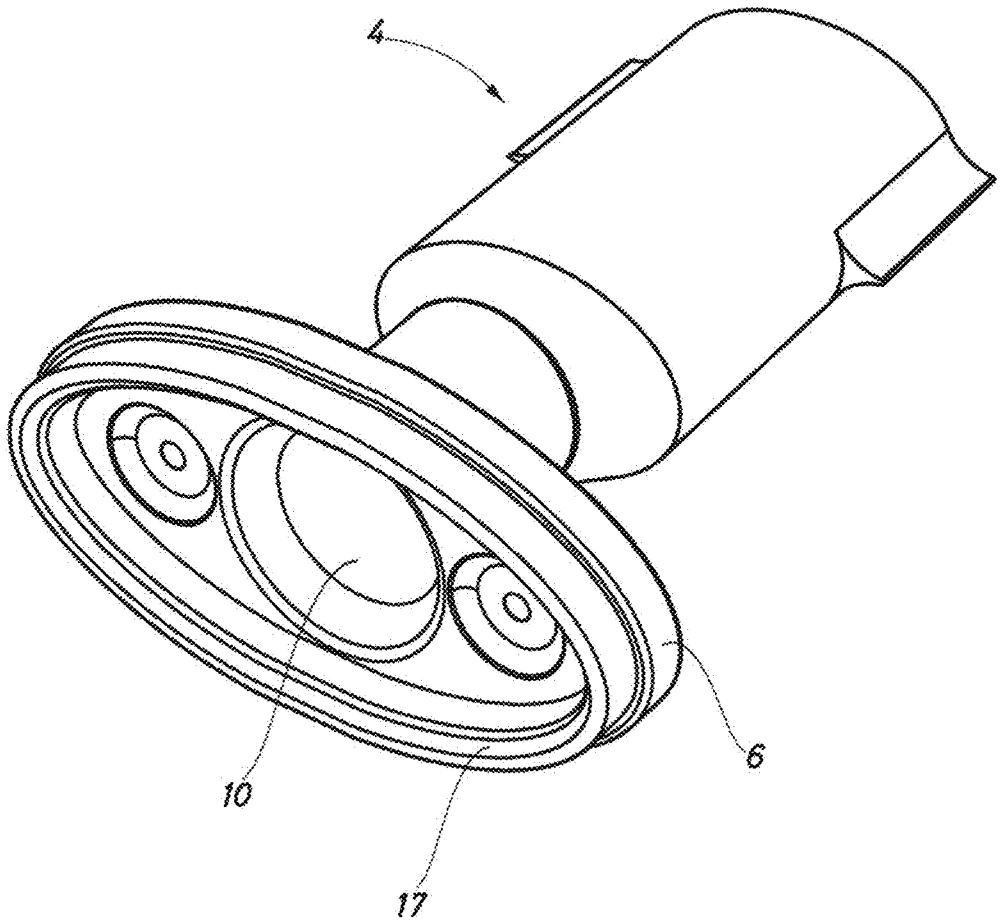
FIG. 11 is a perspective view of a detail of the inlet shown in FIGS. 1 and 9 according to a second embodiment of the conjunction between the lower surface of the cap flange and the upper surface of the inlet flange.

FIGS. 10 and 11 show the cap -3- and the inlet -4-, respectively, in detail. The structural details that can be seen or distinguished in said figures are the same as can be seen in FIG. 9. Thus, in FIG. 10 the cap -3- has an actuation key -9- in the upper portion thereof which can normally be removed or actuated by the user by mechanical action (for example, rotation) when the bag is to be used. Contiguous to said key -9-, the cap -3- comprises an oval-shaped flange -5- which has a continuous recess -16- on the lower surface thereof which runs round said lower surface at the periphery thereof describing the same oval shape as the flange -5-. The flange -5- has a distal cylindrical extension -12- which in turn has a membrane -11- at the end thereof. In FIG. 11, the inlet -4- has an oval-shaped flange -6- which extends in a crown -17- of smaller diameter but also oval (that is, flange -6- of the inlet -4- has a continuous projection on the upper surface thereof which runs round said upper surface at the periphery thereof describing the same oval shape as the flange -6-). There may be additional structures on said upper surface of the flange -6-, for example the two circular recesses that can be seen in FIG. 11 (located between the crown -17- and the channel -10-). Said additional structures meet various design needs, for example to save or optimise materials. Finally, the channel -10- of the inlet -4- can be seen in the centre of the flange -6-.

Figure 12:
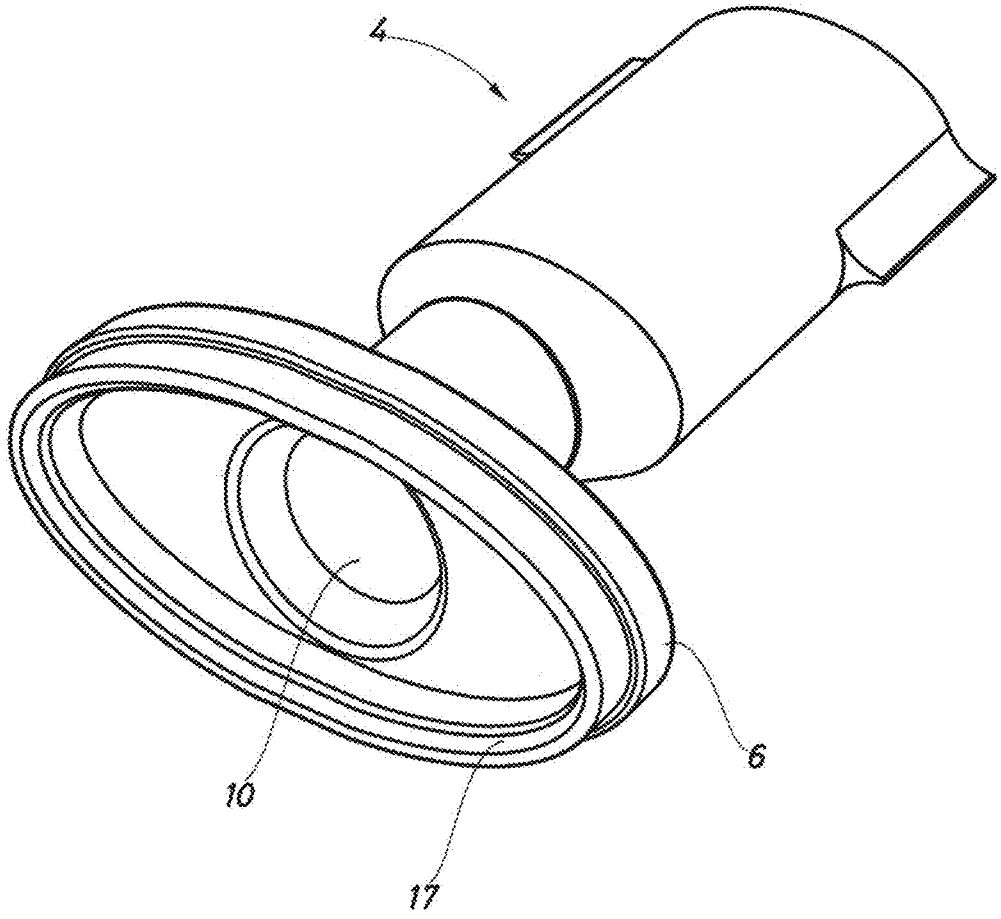
FIG. 12 is a perspective view of a detail of an alternative embodiment of the inlet shown in FIG. 11.

FIG. 12 shows an alternative embodiment of the inlet -4- of FIG. 11 in which the upper surface of the flange -6- does not have the two circular recesses but instead said upper surface is completely conjoined to the lower surface of the flange -5- shown in FIGS. 9 and 10 for the cap -3-. As in the case of FIG. 11, the inlet -4- has on the upper surface of the oval flange -6- a crown -17- of smaller diameter but also oval (that is, the flange -6- of the inlet -4- on the upper surface thereof has a continuous projection which runs round said upper surface at the periphery thereof describing the same oval shape as the flange -6-); and the channel -10- of said inlet can be seen in the centre of the flange -6-.

Figure 13:
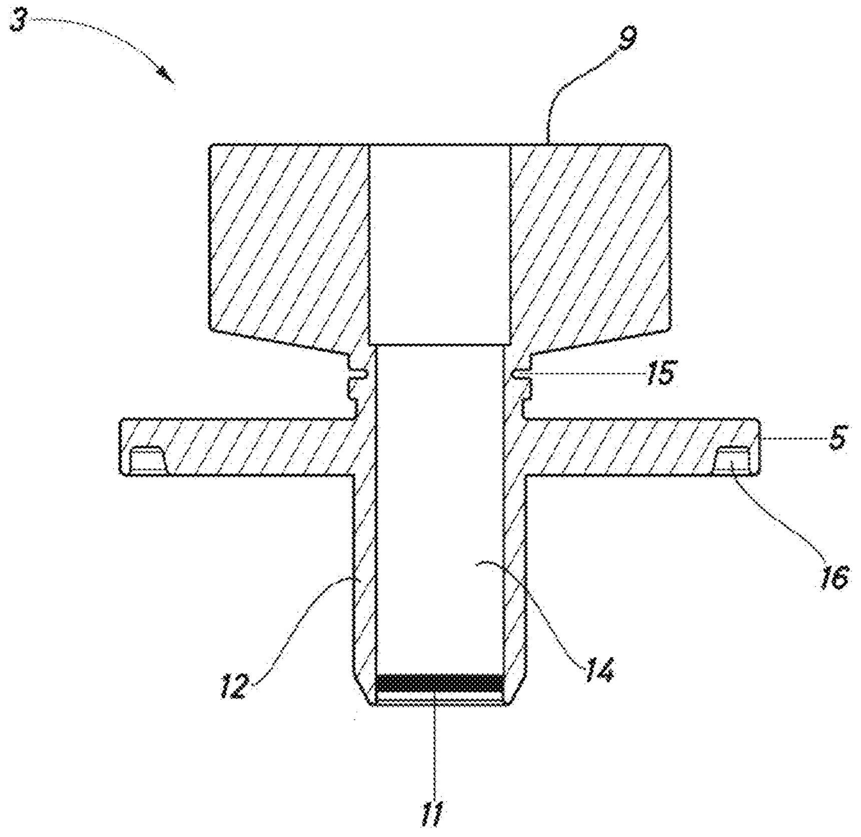
FIG. 13 is a cross section or central transverse section of the cap shown in FIG. 10 in a plane that passes through the semi-major axis of the ellipse described by the flange of said cap.

FIG. 13 shows a cross section or central transverse section of the cap -3- shown in FIG. 10. In FIG. 13, it can be seen that said cap comprises a central cylindrical zone formed by the channel -14- inside the distal cylindrical extension -12- which allows the hermetic closure to be produced between the inlet and the cap. The actuation key -9- is situated on the upper portion of said cylindrical structure which key can be removed by the user by mechanical action (rotation thereof, for example) as mentioned earlier. Said key -9- is connected to the above-mentioned distal cylindrical extension -12- by a weakened zone -15-, that is, a zone where the amount of material in the wall is less and therefore allows easy rotation thereof. As can be seen in FIG. 13, the channel -14- extends inside the key -9- but has a larger diameter. Below said key -9-, after said weakened zone -15-, the flange -5- is situated which has, on the lower surface thereof, the recess -16- (a continuous recess which runs round said lower surface at the periphery thereof describing the same oval shape as the flange -5-). Finally, there is a membrane -11- at the end of the distal cylindrical extension -12-.

Figure 14:
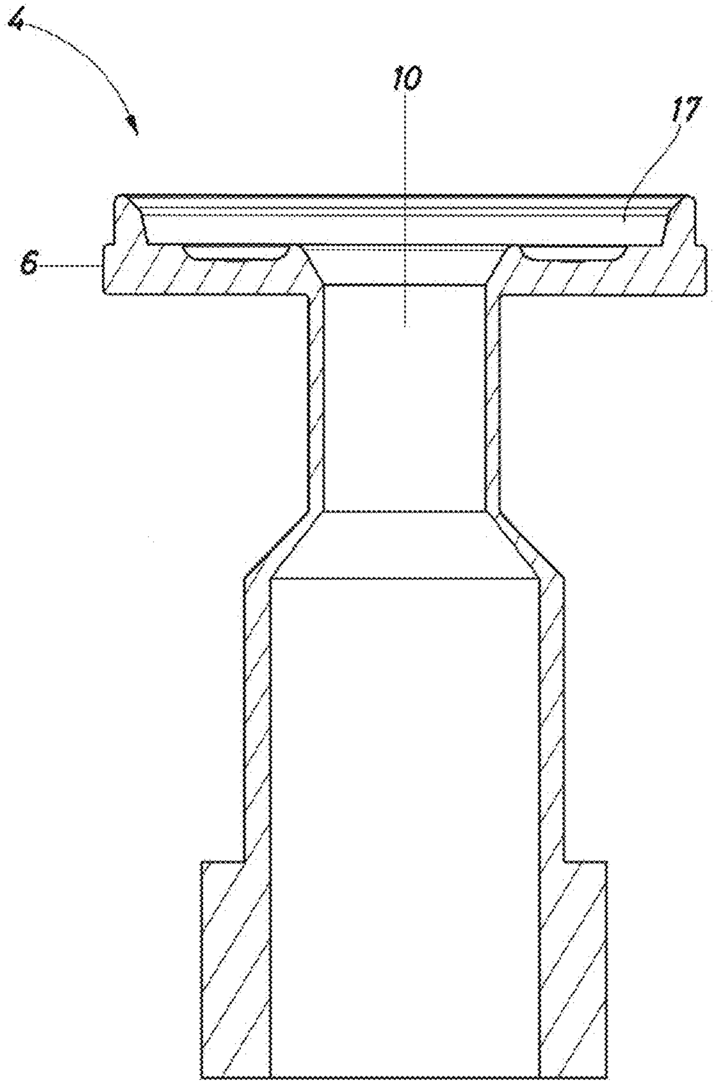
FIG. 14 is a cross section or central transverse section of the inlet shown in FIG. 11 in a plane that passes through the semi-major axis of the ellipse described by the flange of said inlet.

FIG. 14 is a cross section or central transverse section of the inlet -4- shown in FIG. 11 and the same structures or details can therefore be seen as in said FIG. 11. In FIG. 14 it can be seen that the flange -6- of the inlet -4- which extends on the upper surface thereof in a crown -17- of smaller diameter but also oval (that is the flange -6- of the inlet -4- has a continuous projection on the upper surface thereof which runs round said upper surface at the periphery thereof describing the same oval shape as the flange -6-). As mentioned earlier for FIG. 11, there may be additional structures on said upper surface of the flange -6-, for example, the two recesses located between the recess -8- and the channel -10-. Said additional structures meet various design needs, for example to save or optimise material. Finally, the channel -10- of the inlet -4- can be seen in the centre of the flange -6-.

Figure 15:
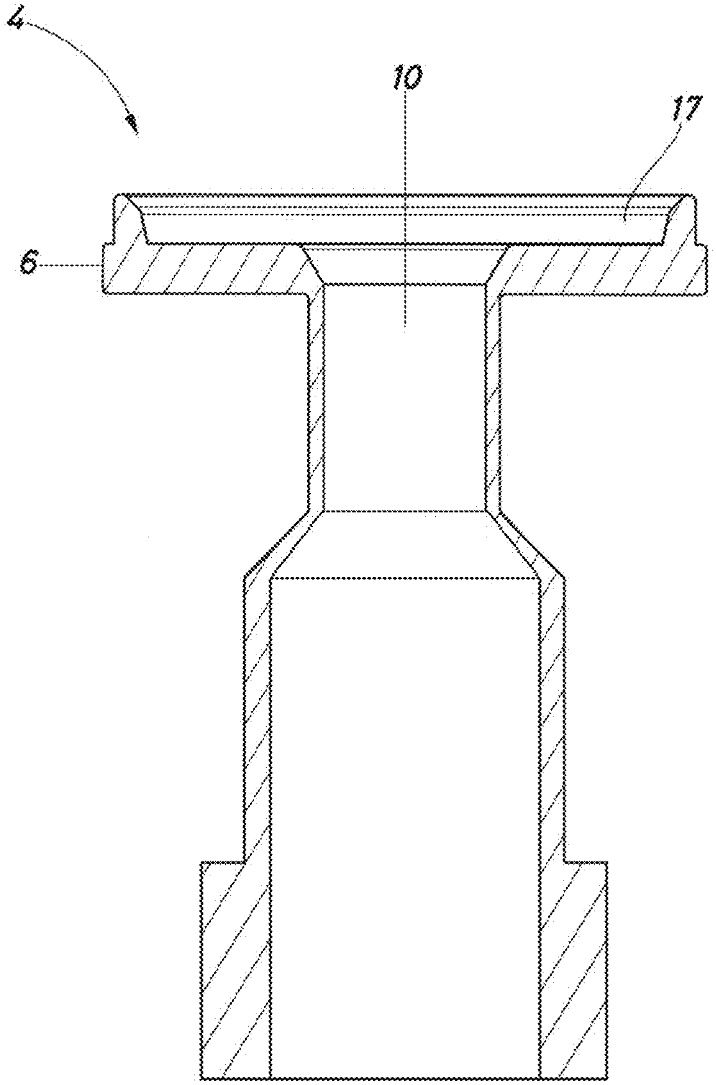
FIG. 15 is a cross section or central transverse section of the inlet shown in FIG. 12 in a plane that passes through the semi-major axis of the ellipse described by the flange of said inlet.

FIG. 15 shows a cross section or central transverse section of the inlet shown in FIG. 12, that is, an alternative embodiment of the inlet compared with the one shown in FIG. 14. As in the case of FIGS. 11 and 12, the only difference between FIGS. 14 and 15 is that the inlet -4- shown in FIG. 15 does not have on the flange -6- the two recesses located between the channel -10- and the crown -17-. The upper surface of the flange -6- shown in FIG. 15 is therefore completely conjoined to the lower surface of the flange -5- shown in FIG. 13.

FIGS. 16 to 20 show general views of the four steps of the method of the present invention for the two embodiments explained in FIGS. 1 to 15.

Figure 16:
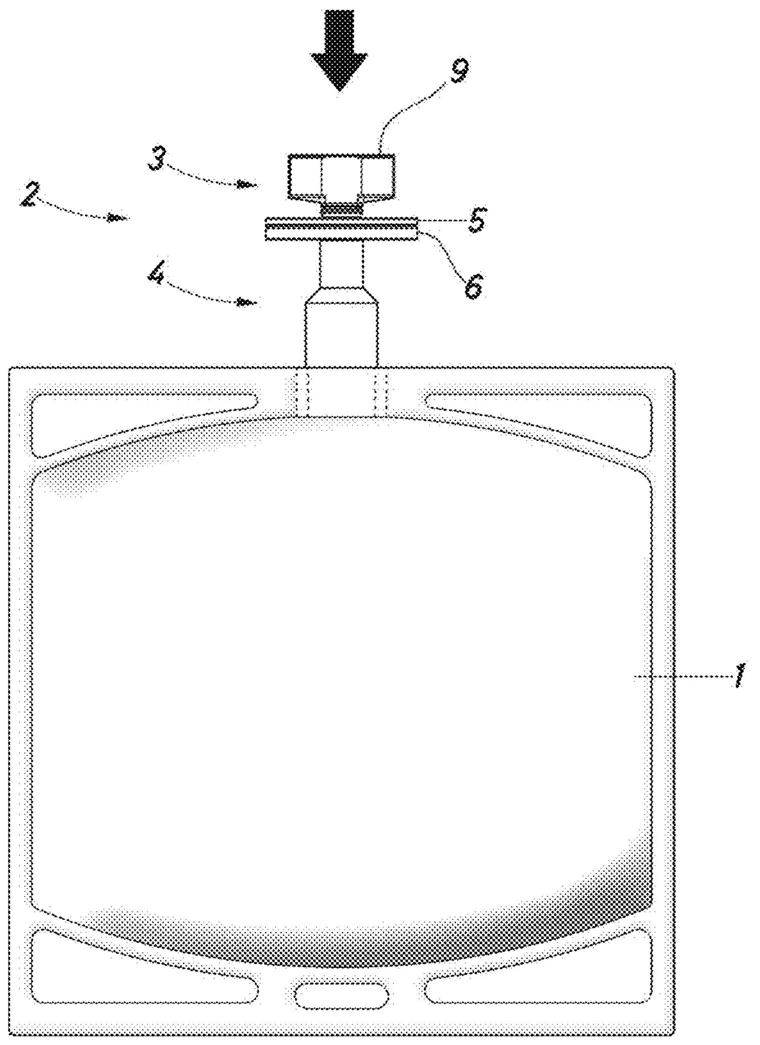
FIG. 16 is a diagrammatic view of the first step (step a)) of the method for the aseptic filling of a bag with a pharmaceutical product or liquid of the present invention. This diagrammatic view may correspond to any of the embodiments which will be explained in greater detail below and which appear in the rest of the figures.

Specifically, FIG. 16 shows the first step (step a)) of the method for the aseptic filling of bags with pharmaceutical products or liquids of the present invention. In this figure the bag -1- with the inlet/cap structure -2- formed by a cap -3- and an inlet -4- can be seen. The wide black arrow with no numeral indicates the action of inserting the cap -3- in the inlet -4- to produce a reversible hermetic closure. In the embodiment shown in FIG. 16, said action or movement consists of a translation in the direction of the central axis of the channel of the inlet, which allows a reversible hermetic closure due to the grip produced between the distal cylindrical extension -12- of the cap -3- and the walls of the channel -10- of the inlet -4-. As explained earlier, the diagrammatic view in FIG. 16 may correspond to any of the embodiments described earlier and shown in FIGS. 1 to 15.

FIG. 17 shows the second step (step b)) of the method for the aseptic filling of bags with pharmaceutical products or liquids of the present invention for a bag with an inlet/cap structure according to the first embodiment, that is, the one shown in FIGS. 2 to 8. FIG. 17 shows how the cap -3- is raised, separating it from the inlet -4- present in the bag -1-, that is, the hermetic closure produced in the first step (step a)) of the method of the present invention (the action denoted by the wide black arrow with no numeral) is opened. When the cap -3- is raised, in this figure, the distal cylindrical extension -12- not visible in FIG. 16 because it is inserted in the channel -10- of the inlet -4- can be seen. The crown -7- of the cap -3- can also be seen in this figure. In FIG. 17, the narrow arrow indicates the action of introducing the pharmaceutical product or liquid concerned into the bag -1-.

FIG. 18 shows the second step (step b)) of the method for the aseptic filling of bags with pharmaceutical products or liquids of the present invention, but in this case for a bag with the inlet/cap structure according to the second embodiment, that is, the one shown in FIGS. 9 to 15. FIG. 18 shows how the cap -3- is raised, separating it from the inlet -4- present in the bag -1-, that is, opening the hermetic closure produced in the first step (step a)) of the method of the present invention (the action denoted by the wide black arrow with no numeral) When the cap -3- is raised, the distal cylindrical extension -12-, which is not visible in FIG. 16 because it is inserted in the channel -10- of the inlet -4-, can be seen. This figure also shows the crown -17- of the inlet -4-. In FIG. 18 the narrow arrow indicates the action of introducing the pharmaceutical product or liquid concerned into the bag -1-.

FIG. 19 shows the third step (step c)) of the method for the aseptic filling of bags with pharmaceutical products or liquids of the present invention. This figure shows that the bag -1- contains a given amount of the pharmaceutical product or liquid concerned (persons skilled in the art will understand that the amount of pharmaceutical product or liquid shown in FIG. 19 may vary widely without affecting the spirit of the present invention). Moreover, in this figure, the wide black arrow with no numeral indicates the action of inserting the cap -3- in the inlet -4- to produce a reversible hermetic closure. As explained earlier, the diagrammatic view of FIG. 19 may correspond to any of the embodiments described earlier and shown in FIGS. 1 to 15.

FIG. 20 shows the fourth step (step d)) of the method for the aseptic filling of bags with pharmaceutical products or liquids of the present invention. This figure shows a bag -1- in which the weld between the flange -5- of the cap -3- and the flange -6- of the inlet -4- has been carried out. This fact can be appreciated due to the smaller distance observed between said flanges compared with that observed when the reversible hermetic closure is produced in the first and third steps (steps a) and c)) of the method of the present invention. As explained earlier, the diagrammatic view of FIG. 20 may correspond to any of the embodiments described earlier and shown in FIGS. 1 to 15.

FIG. 21 shows a cross section or transverse section of a view in detail of the inlet/cap structure -2- seen in the first and third steps of the method of the present invention (steps a) and c)) for a bag with an inlet/cap structure according to the first embodiment, that is, the one shown in FIGS. 2 to 8. This figure shows the inlet/cap structure -2- in the first closure position, that is, producing a reversible hermetic closure in which the distal cylindrical extension -12- of the cap -3- is inserted in the channel -10- of the inlet -4-. It also shows how the crown -7- of flange -5- of the cap -3- makes contact with the recess -8- of the flange -6- of the inlet -4- establishing a contact strip -13-. In this figure, the channel -14- of the cap -3-, of which the continuation with the channel -10- of the inlet -4- is interrupted by the presence of the membrane -11-, can also be seen. Finally, FIG. 21 also shows the actuation key -9- which can be removed by the user by mechanical action (for example, rotation thereof) when the bag is to be used. This figure shows how the reversible hermetic closure produced between the distal cylindrical extension -12- of the cap -3- and the channel -10- of the inlet -4- is positioned between the weld zone (contact strip -13-) and the contents of the bag, thus preventing or contributing to prevent any loose particles produced during the welding process from entering.

FIG. 22 shows a cross section or transverse section of a view in detail of the inlet/cap structure -2- seen in the fourth step of the method of the present invention (step d)), that is, when the cap -3- and the inlet -4- have already been welded at the contact strip -13-, for a bag with the inlet/cap structure according to the first embodiment, that is, the one shown in FIGS. 2 to 8. Said weld is observed by the enclosure or embedding of the crown -7- present on the flange -5- of the cap -3- in the peripheral recess -8- present on the flange -6- of the inlet -4-. The remaining structures that can be seen in this figure are those already explained for FIG. 21.

The insertion or introduction of the distal cylindrical extension -12- of the cap -3- in the channel -10- of the inlet -4-, together with the fact that the weld is produced between the flanges, more preferably on the contact strip -13-, allows to ensure that the pharmaceutical product or liquid introduced into the bag -1- is not contaminated with particles produced or generated during welding.

FIG. 23 shows a cross section or transverse section of a view in detail of the inlet/cap structure seen in the first and third steps of the method of the present invention (steps a) and c)) for a bag with the inlet/cap structure according to the second embodiment, that is, the one shown in FIGS. 9 to 15. The inlet/cap structure -2- is seen in this figure in the first closure position, that is, producing a reversible hermetic closure in which the distal cylindrical extension -12- of the cap -3- is inserted in the channel -10- of the inlet -4-. Additionally, it also shows how the crown -17- of the flange -6- of the inlet -4- makes contact with the recess -16- of the flange -5- of the cap -3- establishing a contact strip -13-. This figure also shows the channel -14- of the cap -3-, of which the continuation with the channel -10- of the inlet -4- is interrupted by the presence of the membrane -11-. Finally, FIG. 23 also shows the actuation key -9- which can be removed by the user by mechanical action (rotation thereof, for example) when the bag is to be used. This figure shows how the reversible hermetic closure produced between the distal cylindrical extension -12- of the cap -3- and the channel -10- of the inlet -4- is positioned between the weld zone (contact strip -13-) and the contents of the bag, thus preventing or contributing to prevent any loose particles produced during the welding process from entering.

FIG. 24 shows a cross section or transverse section of a view in detail of the inlet/cap structure -2- seen in the fourth step of the method of the present invention (step d)), that is, when the cap -3- and the inlet -4- have already been welded at the contact strip -13-, for a bag with the inlet/cap structure according to the second embodiment, that is, the one shown in FIGS. 9 to 15. Said weld can be seen by the enclosure or embedding of the crown -17- present on the flange -6- of the inlet -4- in the peripheral recess -16- of the flange -5- of the cap -3-. The rest of the structures that can be seen in this figure are those already explained for FIG. 23.

The insertion or introduction of the distal cylindrical extension -12- of the cap -3- in the channel -10- of the inlet -4-, together with the fact that the weld is produced between the flanges, more preferably at the contact strip -13- ensures that the pharmaceutical product or liquid introduced into the bag -1- is not contaminated with particles produced or generated during welding.

The invention claimed is:

1. A bag with inlet/cap structure comprising:

a cap with an oval cap flange extending laterally from the cap, and with a distal cylindrical extension that extends laterally from the cap and beyond the cap flange;

a bag with an inlet, wherein the inlet comprises an inlet flange extending laterally from the inlet, and an inlet channel extending vertically through the inlet, wherein the distal cylindrical extension is inserted into the inlet channel, wherein the inlet channel forms a hermetic seal with the distal cylindrical extension when inserted therein;

an upper surface on the inlet flange;

a lower surface on the cap flange;

a membrane at a distal end of the distal cylindrical extension;

an annular continuous projection at or near a periphery of the cap flange or the inlet flange; and an annular continuous recess at or near the periphery of the cap flange when the inlet flange has the annular projection, or at or near the periphery of the inlet flange when the cap flange has the annular projection.

2. The inlet/cap structure according to claim 1, wherein the lower surface on the cap flange and the upper surface on the inlet flange are totally or partially conjoined.

3. The inlet/cap structure according to claim 1, wherein the annular continuous projection is on the lower surface of the cap flange, and the annular continuous recess is on the upper surface of the inlet flange.

4. The inlet/cap structure according to claim 1, wherein the annular continuous recess is on the lower surface of the cap flange, and the annular continuous projection is on the upper surface of the inlet flange.

5. The inlet/cap structure according to claim 1, further comprising the cap inserted in the inlet of the bag, and wherein the annular continuous projection and the annular continuous recess form a contact strip.

6. The inlet/cap structure according to claim 1, wherein the inlet flange and cap flange are of an equivalent shape and are of an equivalent or approximately equivalent size.

7. The inlet/cap structure according to claim 1, wherein the inlet flange and the cap flange are both oval in shape.

8. The inlet/cap structure according to claim 1, wherein the lower surface of the cap flange extends parallel to and is separated from the upper surface of the inlet flange.

9. The inlet/cap structure according to claim 1, wherein the lower surface of the cap flange extends parallel to and abuts against the upper surface of the inlet flange.

10. The inlet/cap structure according to claim 1, wherein the annular continuous projection fully encloses the annular continuous recess.

11. The inlet/cap structure of claim 1, further comprising a weld between the cap and the inlet, wherein said weld causes a reversible hermetic closure position to become an irreversible hermetic closure position.

12. The inlet/cap structure of claim 1, wherein the inlet/cap structure has a reversible hermetic closure position.

* * * * *